United States Patent [19]

Poindexter et al.

[11] Patent Number: 5,668,151
[45] Date of Patent: Sep. 16, 1997

[54] DIHYDROPYRIDINE NPY ANTAGONISTS: PIPERIDINE DERIVATIVES

[75] Inventors: Graham S. Poindexter, Old Saybrook; Marc Bruce, Wallingford; Graham Johnson, Madison; Karen LeBoulluec; Charles P. Sloan, both of Wallingford, all of Conn.

[73] Assignee: Bristol-Myers Squibb Company, New York, N.Y.

[21] Appl. No.: 639,968

[22] Filed: May 8, 1996

Related U.S. Application Data

[63] Continuation-in-part of Ser. No. 482,353, Jun. 7, 1995, abandoned.

[51] Int. Cl.$^6$ ............... A61K 31/445; C07V 211/86
[52] U.S. Cl. ............... 514/318; 514/332; 546/194; 546/263
[58] Field of Search ............... 514/318, 332, 514/333, 335; 546/194, 261, 263

[56] References Cited

U.S. PATENT DOCUMENTS

| | | | |
|---|---|---|---|
| 4,707,486 | 11/1987 | Flockerzi et al. | 514/318 |
| 4,782,160 | 11/1988 | Fujikura et al. | 546/321 |
| 4,829,076 | 5/1989 | Szilágyi et al. | 514/356 |

FOREIGN PATENT DOCUMENTS

| | | |
|---|---|---|
| 0533504 | 3/1993 | European Pat. Off. . |
| 0534520 | 3/1993 | European Pat. Off. . |
| 9301686 | 8/1994 | France . |
| JO4049-237-A | 2/1892 | Japan . |

OTHER PUBLICATIONS

Serradeil–LeGal et al, *Society for Neuroscience*, 1994, abstract No. 376.14.

Rudolf et al, *European Journal of Pharmacology*, 1994, 271, R11–13.

*Primary Examiner*—C. Warren Ivy
*Assistant Examiner*—Garth M. Dahlen
*Attorney, Agent, or Firm*—Richard P. Ryan

[57] ABSTRACT

A series of non-peptidergic antagonists of NPY have been synthesized and are comprised of piperidine and tetrahydropyridine derivatives of 4-phenyl-1,4-dihydropyridines of Formula I.

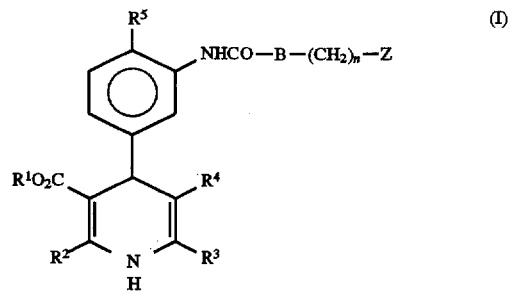

As antagonists of NPY-induced feeding behavior, these compounds are expected to act as effective anorexiant agents in promoting weight loss and treating eating disorders.

15 Claims, No Drawings

DIHYDROPYRIDINE NPY ANTAGONISTS: PIPERIDINE DERIVATIVES

CROSS REFERENCE TO RELATED APPLICATION

This is a continuation-in-part of patent application U.S. Ser. No. 08/482,353 filed Jun. 7, 1995 and now abandoned.

BACKGROUND OF THE INVENTION

The present invention concerns heterocyclic carbon compounds comprising 4-phenyl-1,4-dihydropyridines with a piperidinyl- or tetrahydropyridinyl-containing moiety attached to the 3-position of the 4-phenyl ring. These compounds act as NPY antagonists.

A substantial body of art has accumulated over the past two decades with respect to 4-aryl-1,4-dihydropyridine compounds. A large number of these possess calcium antagonist properties and find utility in the treatment of cardiovascular diseases. Several 4-aryl-1,4-dihydropyridines with piperidine-ring-containing-substituents have been reported.

A series of compounds of formula (1) was claimed to be

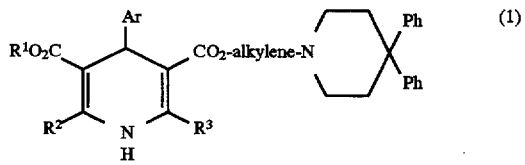

useful as vasodilators, antihypertensives and diuretics in U.S. Pat. No. 4,707,486.

A series of dihydropyridines, including compounds of formula (2), were disclosed and claimed to have antitumor promoting

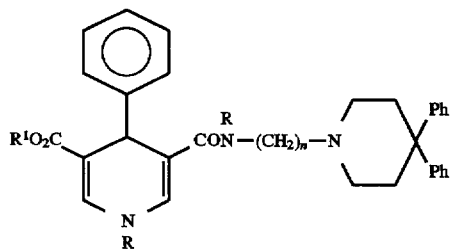

activity in European Patent Application 533,504.

European Patent Application 534,520 discloses related compounds having formula (3) wherein $R^5$ is alkyl, phenyl and aralkyl.

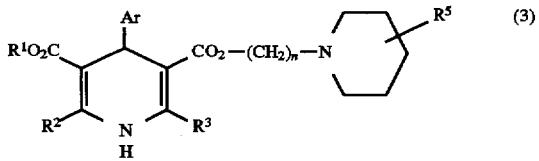

A compound of formula (4) has been disclosed in JO 4049-237-A and claimed to be an inhibitor of Phospholipase $A_2$.

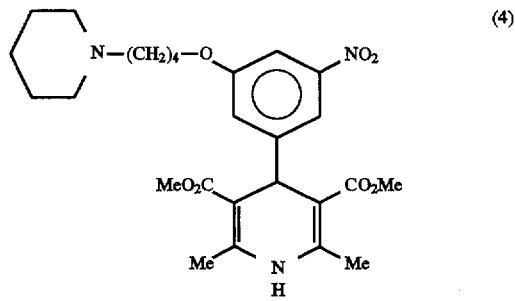

Of less significance is a series of antihypertensive dihydropyridine anilide derivatives disclosed in U.S. Pat. No. 4,829,076 and containing compounds of formula (5)

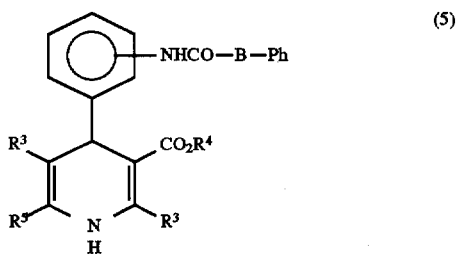

in which B is a chemical bond or an alkylene group.

These reference compounds are readily distinguished structurally from the compounds of the instant invention by virtue of many of the art compounds having the piperidine substituents attached to the dihydropyridine ring itself as well as by the nature of most of the linking functional groups, e.g. oxyalkylenyl and carboxylate groups. In contrast, compounds of the instant invention contain an alkylenylpiperidine moiety attached to the 3-position of the 4-phenyl ring by means of an anilide, urethane or urea connection. Not only are the present compounds structurally novel, they also have been discovered to possess novel NPY antagonist activity while having greatly reduced calcium antagonist properties.

In summary, the prior art does not disclose nor suggest the unique combination of structural fragments which embody these novel dihydropyridine derivatives as having good antagonist activity at NPY $Y_1$ receptor sites and reduced cardiovascular effects.

Neuropeptide Y (NPY) is a 36 amino acid peptide first isolated in 1982 from porcine brain.[1,2] The peptide is a member of a larger peptide family which also includes peptide YY (PYY), pancreatic peptide (PP), and the non-mammalian fish pancreatic peptide Y (PY). Neuropeptide Y is very highly conserved in a variety of animal, reptile and fish species. It is found in many central and peripheral sympathetic neurons and is the most abundant peptide observed in the mammalian brain. In the brain, NPY is found most abundantly in limbic regions. The peptide has been found to elicit a number of physiological responses including appetite stimulation, anxiolysis, hypertension, and the regulation of coronary tone.

Structure-activity studies with a variety of peptide analogs (fragments, alanine replacements, point mutations, and internal deletion/cyclized derivatives) suggest a number of receptor subtypes exist for NPY.[2b] These currently include the $Y_1$, $Y_{1-like}$, $Y_2$, $Y_3$, and the $Y_4$ subtypes.

Although specific peptidic antagonists have been identified for most of the subtypes, few selective non-peptidic antagonists have been reported to date. Several competitive but non-selective, non-peptidic antagonists are known, however (Chart 1). The heterocyclic guanidine derivative He 90481 (4) was found to be a weak but competitive antagonist of NPY-induced $Ca^{++}$ entry in HEL cells ($pA_2$=4.43).[3] The compound was also found to have $\alpha_2$-adrenergic and histaminergic activity at this dose range. D-Myo-inositol-1,2,6-triphosphate (5) was reported to be a potent but non-competitive antagonist to NPY-induced contractions in guinea pig basilar artery.[4] Similarly, the benextramine-like bisguanidines 6a and 6b were reported to displace $^3$H-NPY in rat brain ($IC_{50}$, 19 and 18.4 µM) and to display functional antagonism in rat femoral artery.[5] The bisguanidine 6b was shown to be functionally selective for the $Y_2$ receptor since it antagonized the effect of the $NPY_2$ agonist $NPY_{13-36}$ but had no effect on the vasoconstrictive activity of the $NPY_1$ agonist [Leu$^{31}$, Pro$^{34}$]NPY.[5c]

Dipeptide-like sulfonamidoyl amidine derivatives of formula (7)

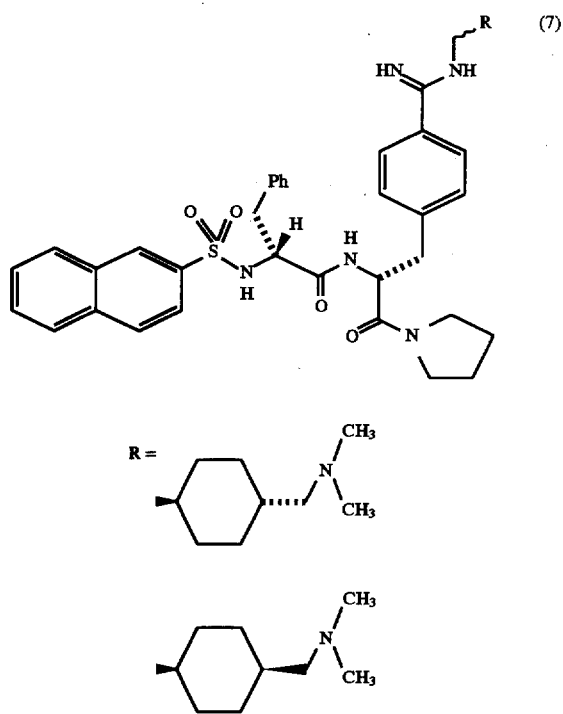

have been disclosed as selective NPY $Y_1$ antagonists. See: French Patent 9,301,686; Serradeil-LeGal, et al., *Society for Neuroscience*, 1994, abstract no. 376.14.

A guanidine derivative of formula (8) having NPY $Y_1$ selective receptor antagonist activity was

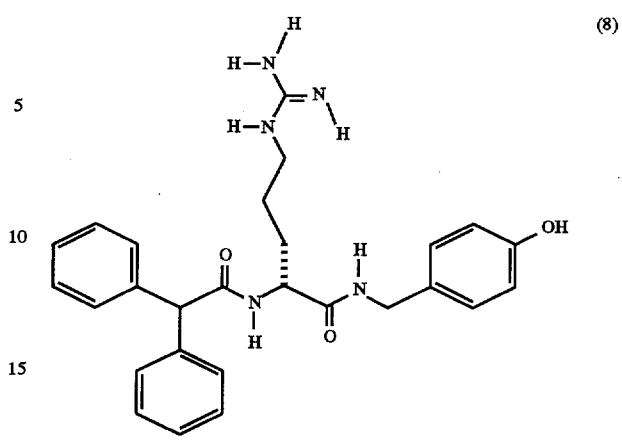

disclosed by Rudolf, et al., *Eur. J. Pharmacology*, 1994, 271, R11–13.

In sum, the compounds of this invention may be distinguished over compounds of the prior art on the basis of molecular structure and biologic activity. There is nothing in the prior art that anticipates or suggests the novel NPY antagonists of the present invention.

SUMMARY AND DETAILED DESCRIPTION OF THE INVENTION

The present invention comprises the compounds of Formula I,

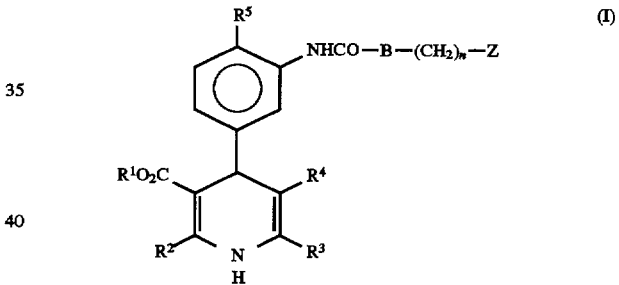

their pharmaceutically acceptable acid addition salts and/or their hydrates thereof. In the foregoing structural formula, the symbols $R^1$–$R^5$, B and Z have the following meanings.

$R^1$ is lower alkyl; methyl being preferred.

$R^2$ and $R^3$ are independently selected from cyano and lower alkyl, with methyl being preferred.

$R^4$ is selected from —$CO_2R^1$, cyano and

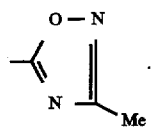

$R^5$ can be hydrogen, halogen, hydroxy, lower alkyl, lower alkoxy, and lower alkenyloxy such as allyloxy.

B is NH, NR¹, O, or a chemical bond.

The symbol n is an integer from 2 to 5 with 3 being preferred.

Finally, Z is

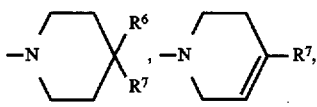

or a quaternary piperidinium salt or quaternary 1,2,3,6-tetrahydropyridinium salt, wherein the quaternary piperidinium salt is

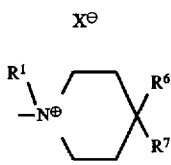

and the quaternary tetrahydropyridinium salt is

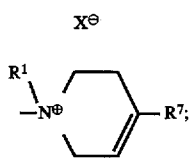

with $X^\ominus$ being chloride, bromide, or iodide;
$R^6$ is hydrogen, hydroxy or cyano; and
$R^7$ is $C_{3-7}$ cycloalkyl,

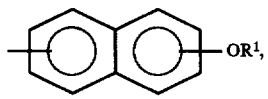

and

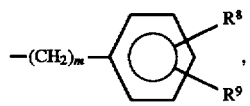

with m being zero or an integer from 1 to 4; and $R^8$ and $R^9$ being independently selected from hydrogen, lower alkyl, $C_{3-7}$ cycloalkyl, lower alkoxy, lower alkenyloxy, lower alkynyloxy, hydroxy, phenyl, phenoxy, $NH_2$, $NHCOR^1$, $CO_2R^1$, $NO_2$ and trifluoromethyl.

The term "lower" indicates that the alkyl, alkoxy, alkenyloxy or alkynyloxy group contains from one to four carbon atoms. Preferred compounds of the instant invention are Formula I compounds wherein $R^2$ and $R^3$ are methyl; $R^4$ is —$CO_2Me$; $R^5$ is hydrogen; B is NH; and $R^7$ is an aromatic ring-containing moiety. Most preferred compounds are those wherein $R^7$ is selected from substituted phenyl, particularly with alkoxy substituents and cyclohexyl.

The compounds of the present invention can exist as optical isomers and both the racemic mixtures of these isomers as well as the individual optical isomers themselves are within the scope of the present invention. The racemic mixtures can be separated into their individual isomers through well known techniques such as the separation of the diastereomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, dichloroacetic acid, tartaric acid, lactic acid, succinic acid, citric acid, maleic acid, fumaric acid, sorbic acid, aconitic acid, salicylic acid, phthalic acid, enanthic acid, and the like.

The Formula I compounds can also be quaternized by standard techniques to yield quaternary piperidinium or tetrahydpyridinium salt products of Formula I. Quaternization would be expected to maximize the peripheral effects of Formula I compounds and minimize brain penetration.

The compounds of the present invention may be produced by the following processes which employ variations of the Hantzsch synthetic reaction applied to the appropriate starting materials. General processes for preparing Formula I compounds are outlined in Schemes 1 and 2. The symbols $R^1$–$R^5$, B, n and Z are as previously defined, and X is chloro, bromo or iodo. The dihydropyridine intermediate (V) can be prepared by the reaction of 3-nitrobenzaldehyde and the requisite acetoacetates, such as compound (VI) wherein $R^4$ is e.g. carbethoxy, under standard Hantzsch condensation conditions[6] (e.g. ammonium acetate in refluxing isopropanol) if symmetrical intermediates of Formula (V) are desired. Symmetrical intermediate (V) compounds would have $R^2=R^3$ and $R^4$=—$CO_2R^1$. Unsymmetrical dihydropyridines (V) are obtained using modified Hantzsch conditions starting with Knoevenagel adducts (VII)[7] and the appropriate dicarbonyl compounds (VI). A number of these dihydropyridines (V) have been described in the literature[8].

Reduction of intermediate (V) compounds using catalytic reduction, an iron reduction method (Fe/$NH_4Cl$/aq. alcohol[15]) or a Ni(OAc)$_2$/NaBH$_4$ exchange resin procedure[9] provides the amino intermediate (IV). A number of these aniline derivatives have also been described in the literature[10]. In Scheme 1, Formula I compounds in which B is a covalent bond, are synthesized. Reaction of (IV) with a haloacyl halide (VIII) gives compound (III), which is then treated with H—Z (a piperidinyl or tetrahydropyridinyl compound of formula (X)) to yield the desired Formula I product, with the piperidine moiety linked via an anilide group. A modified route beginning with compound (IV) and proceeding via intermediates (XXII) and (XXI) gives a Formula I product in which n is 4.

Formula I compounds having a urea linkage are synthesized as in Scheme 2. In process A, reaction of (IV) with a haloalkyl isocyanate (IX) gives compound (II) which is then reacted with compound (X) to provide the Formula I product. In process B, compound (IV) is converted, via the carbamate (XXIV), to the isocyanate intermediate (XXXIV). Subsequent reaction with intermediate (XX), readily produced from compound (X) as shown, yields Formula I: B=NH product.

Certain intermediates of Formula (V) require modified syntheses and some of these are exemplified in Scheme 3. Synthesis A shows hydrolysis of an acetal derivative (XIII) following a general synthetic route similar to that reported by Satoh.[11] Hydrolysis of the acetal (XIII) was accomplished by acid treatment (HCl/acetone). The resulting aldehyde (XII) was converted to the oxime derivative via reaction with hydroxylamine in acetic acid and then was dehydrated by heating in acetic anhydride to produce the cyano-substituted intermediate (V). Conversion of such a cyano-substituted nitrobenzene compound (V) to the corresponding cyano-substituted aniline intermediate (IV) can be accomplished with Fe/NH$_4$Cl in alcohol.

Synthesis B outlines preparation of oxadiazole substituted intermediates. A dihydropyridine carboxylic acid starting material (XIV) is coupled with acetamidoxime via carbonyldiimidazole (CDI) and then heated at about 200° to convert the intermediary oxime ester to the oxadiazole nitro compound (V). Reduction of (V) to the oxadiazole substituted aniline compound (IV) is carried out using the iron method in order to preclude N—O bond cleavage seen with hydrogenolysis.

Substituted piperidines and tetrahydropyridines (X) are commercially available and/or described in the chemical literature. A reaction flow diagram (Synthesis A) gives convenient syntheses for H—Z intermediates in Scheme 4. The 4-piperidone intermediate (XVI) is treated with an appropriate R$^7$-lithium reagent to provide the hydroxy intermediate compound (XV). This hydroxy intermediate is readily converted into the reaction intermediates (Xa), (Xb) or (Xc). Initial dehydration of (XVa) with p-toluenesulfonic acid followed by hydrogenation over Pd(OH)$_2$ (Pearlman's catalyst) gives the piperidine intermediate (Xa). Acidic hydrogenation of (XVa) using palladium on carbon catalyst provides the 4-hydroxy intermediate (Xb). Treatment of the t-BOC intermediate (XVb) with trifluoroacetic acid yields the tetrahydropyridine intermediate (Xc).

Synthesis B of Scheme 4 demonstrates preparation of specific compound (X) intermediates. Preparation of other compound (X) products by means of different syntheses would be known to one skilled in organic chemical synthesis. Using the method of Williams[12], aromatic substitution of phenoxide provides intermediate (XVIII) which is reacted with 1-benzyl-4-piperidone in the presence of n-BuLi to provide the N-benzyl intermediate (XVa) via metal-halogen exchange. Debenzylation by hydrogenation affords the desired intermediate (Xb) wherein R$^7$ is 2-phenoxyphenyl.

Sequence 2 illustrates a series of conversions of compound (X) intermediates.

For products wherein R$^5$ is other than hydrogen, the reaction sequence begins using the appropriate R$^5$-substituted nitrobenzaldehyde except when R$^5$ is hydroxy. In this case, an intermediate (V) compound, wherein R$^5$ is hydroxy, is O-allylated by treatment with NaH/allyl bromide to give an intermediate (V) compound wherein R$^5$ is allyloxy, as shown in Scheme 5. Iron reduction provides the aniline intermediate (IV) which is reacted according to a process of Schemes 1 and 2 to provide the Formula I compound wherein R$^5$ is allyloxy. Deprotection is achieved using PdCl$_2$ in a HOAc/NaOAc buffer to yield the R$^5$—OH Formula I product.

Basic Formula I products are also convertible into quaternary salts using standard amine quaternization techniques, e.g. alkylation of the piperidine or tetrahydropyridine moiety with an alkyl halide (see: Scheme 6).

Additional reaction intermediates and Formula I products can be prepared by appropriate modification of the foregoing synthetic schemes and procedures. Such modifications would be obvious to practitioners skilled in the chemical art. Additional examples and experimental procedures are provided infra.

The compounds of this invention demonstrate binding affinity at NPY Y$_1$ receptors. This pharmacologic activity is assayed in SK-N-MC (human neuroblastoma) cell membranes using iodine-125 labeled I-PYY as a radioligand. The compounds of this invention had good binding affinities as evidenced by IC$_{50}$ values being about 10 µM or less at NPY Y$_1$ receptors. Preferred compounds have IC$_{50}$ values less than 100 nM and most preferred compounds have IC$_{50}$ values of less than 10 nM. Although as a class, these types of dihydropyridines have significant affinity for $\alpha_1$-adrenergic receptors and/or Ca$^{++}$ channels, the compounds of this invention possess much weaker affinities for $\alpha_1$ adrenergic receptors and Ca$^{++}$ channels. As such, these compounds act as selective NPY antagonists at NPY Y$_1$ receptor sites. There is evidence that NPY contributes to certain symptoms in these disorders: hypertension, eating disorders, and depression/anxiety;[13] as well as circadian rhythms. Compounds of this invention are expected to be useful in treating these disorders as well as sleep disturbance and diabetes.

Selected compounds are tested further for their ability to block NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a Formula I compound or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat hypertension, depression, diabetes and anxiety disorders.

Therapeutically, the instant compounds are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethelene glycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C. when not specified.

The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), triplet (t) doublet of doublets (dd), quartet (q) or pentuplet (p). Abbreviations employed are DMSO-$d_6$, (deuterodimethylsulfoxide), $CDCl_3$ (deuterochloroform), and are otherwise conventional. The infrared (IR) spectral descriptions include only absorption wave numbers ($cm^{-1}$) having functional group identification value. The IR determinations were generally employed using potassium bromide (KBr) as diluent. The elemental analyses are reported as percent by weight.

A. PREPARATION OF INTERMEDIATES

1. Formula (VII) Compounds

EXAMPLE 1

General Procedure for the Preparation of Knoevenagel Adducts (VII)

Following a general method reported by Jones[7], a mixture of 300 mmol each of 3-nitrobenzaldehyde and the requisite $\beta$-keto ester was dissolved in 250 mL of toluene and piperidine (2.5 mL) and glacial HOAc (5 mL) were added. The solution was then allowed to reflux several h during which time the theoretical amount of $H_2O$ was removed by a Dean-Stark trap. The toluene was then removed in vacuo and the resulting Knoevenagel products purified by flash chromatography ($SiO_2$: EtOAc/Hex) or crystallization.

EXAMPLE 2

3-(3-Nitrophenyl)-2-(1-oxobutyl)-2-propenoic acid, ethyl ester

The yellow oil was isolated as a mixture of E and Z isomers in 47% yield: $^1$H NMR ($CDCl_3$) $\delta$8.23 (m, 2H), 7.52 (m, 3H), 4.32 (m, 2H), 2.67 and 2.53 (t, 2H, J=7.2 Hz), 1.66 (m, 2H), 1.29 (m, 3H), and 0.97 and 0.87 (t, 3H, J=7.4 Hz). Anal. Calcd for $C_{15}H_{17}NO_5$: C, 61.85; H, 5.88; N, 4.81. Found: C, 61.76; H, 5.86; N, 4.82.

EXAMPLE 3

2-(Dimethoxyacetyl)-3-(3-nitrophenyl)-2-propenoic acid, ethyl ester

This adduct was isolated as an orange oil in 34% yield: $^1$H NMR ($CDCl_3$) $\delta$8.34–8.23 (m, 2H), 7.99–7.70 (m, 3H), 4.94–4.93 (m, 1H), 4.30–4.22 (m, 2H), 3.79 (d, 1H, J=8 Hz), 3.35–3.33 (m, 6H), 1.28–1.13 (m, 3H). Anal. Calcd. for $C_{15}H_{17}NO_7$: C, 55.73; H, 5.30; N, 4.33. Found: C, 55.28; H, 4.84; N, 4.59.

2. Formula V, XII, and XIII Intermediates

EXAMPLE 4

General Method for the Preparation of Dihydropyridine Intermediates (V)

For the symmetrical dihydropyridines of Formula V, the requisite $\beta$-keto ester (126 mmol), 3-nitrobenzaldehyde (63 mmol), and $NH_4OAc$ (95 mmol) were refluxed for several h in 150 mL of EtOH or i-PrOH using standard Hantzsch conditions[6]. The crude reaction mixture was cooled to ambient temperature and the volatiles removed in vacuo. The symmetrical dihydropyridines were crystallized from EtOH or i-PrOH. Generally, for the asymmetrical Formula (V) intermediate, a mixture of the requisite Knoevenagel adduct (VII) (70 mmol) and methyl 3-aminocrotonate (70 mmol) was refluxed in i-PrOH overnight (24 h). The volatiles were then removed in vacuo and the crude products recrystallized from EtOH.

EXAMPLE 5

1,4-Dihydro-2-methyl-4-(3-nitrophenyl)-6-propyl-3, 5-pyridinedicarboxylic acid, ethyl[5] methyl[3] ester The compound was obtained as a bright yellow solid in 34% yield; mp 102°–105° C.; $^1$H NMR ($CDCl_3$) $\delta$8.09 (t, 1H, J=2 Hz), 7.99–7.96 (m, 1H), 7.63–7.59 (m, 1H), 7.35 (t, 1H, J=8 Hz), 5.77 (br s, 1H), 4.14–3.99 (m, 2H), 3.63 (s, 3H), 2.77–2.61 (m, 2H), 2.34 (s, 3H), 1.72–1.53 (m, 2H), 1.20 (t, 3H, J=7 Hz), 0.97 (t, 3H, J=7.4 Hz). Anal Calcd. for $C_{20}H_{24}N_2O_6 \cdot 0.2H_2O$: C, 61.43; H, 6.03; N, 7.16. Found: C, 61.57; H, 6.14; N, 7.09.

EXAMPLE 6

1,4-Dihydro-2-methyl-6-(dimethoxymethyl)-4-(3-nitrophenyl)-3,5-pyridinedicarboxylic acid, ethyl[5] methyl[3] ester (XIII)

The compound was obtained in 35% yield after purification by flash chromatography ($SiO_2$: EtOAc/Hex): mp 118°–122° C.; $^1$H NMR ($CDCl_3$) δ8.14 (t, 1H, J=2 Hz), 8.02–7.99 (m, 1H), 7.65–7.61 (m, 1H), 7.38 (t, 1H, J=8 Hz), 6.82 (br s, 1H), 6.03 (s, 1H), 5.13 (s, 1H), 4.17–4.06 (m, 2H), 3.64 (s, 3H), 3.48 (s, 3H), 3.43 (s, 3H), 2.38 (s, 3H), 1.24 (t, 3H, J=7 Hz); $^{13}$C NMR ($CDCl_3$) δ167.4, 166.0, 149.3, 148.3, 145.1, 143.9, 134.2, 128.8, 122.9, 121.5, 104.7, 102.5, 98.5, 60.4, 55.7, 55.1, 51.2, 40.0, 19.7, 14.1. Anal Calcd. for $C_{20}H_{24}N_2O_8$: C, 57.14; H, 5.75; N, 6.66. Found: C, 57.07; H, 5.64; N, 6.64.

EXAMPLE 7

1,4-Dihydro-2,6-dimethyl-4-(3-nitrophenyl)-3,5-pyridinedicarboxylic acid, n-butyl methyl ester A solution of n-butyl acetoacetate (0.10 mole), methyl 3-aminocrotonate (0.10 mole), 3-nitrobenzaldehyde (0.10 mole) and 150 mL of i-PrOH was refluxed overnight (18 h). The volatiles were removed in vacuo and the residue purified by flash chromatography ($SiO_2$: EtOAc/Hex) to furnish the product in 49% yield as low melting, yellow solid: mp 69°–70° C. Anal. Calcd for $C_{20}H_{24}N_2O_6$: C, 61.85; H, 6.23; N, 7.21. Found: C, 62.02; H, 6.21; N, 6.95.

EXAMPLE 8

2-Cyano-1,4-dihydro-6-methyl-4-(3-nitrophenyl)-3,5-pyridinedicarboxylic acid, ethyl[3] methyl[5]-ester The acetal intermediate of Example 6 (XIII) (24 mmol) was taken up in 80 mL of acetone and 6N HCl (8 mL) was added. After stirring at ambient temperature for 1.5 h, the solvent was removed in vacuo. The resulting solid was rinsed with one portion of $H_2O$ and then filtered. Purification by flash chromatography ($SiO_2$: EtOAc/Hex) furnished the formyl derivative (XII) in 88% yield as an orange solid: mp 111°–114° C.; $^1$H NMR ($CDCl_3$) δ8.12–8.01 (m, 2H), 7.61–7.46 (m, 1H), 7.41 (t, 1H, J=8 Hz), 7.04 (br s, 1H), 5.23–5.22 (m, 1H), 4.30–4.14 (m, 2H), 3.77 (s, 1H), 3.64 (s, 3H), 2.43 (s, 3H), 1.28 (t, 3H, J=7 Hz); $^{13}$C NMR ($CDCl_3$), δ186.5, 167.0, 165.2, 148.4, 147.6, 145.2, 139.0, 134.2, 129.3, 123.0, 122.1, 115.0, 101.9, 61.6, 51.4, 40.7, 19.6, 14.1. Anal. Calcd. for $C_{18}H_{18}N_2O_7$: C, 57.75; H, 4.85; N, 7.48. Found: C, 57.61; H, 4.60; N, 7.33.

The formyl intermediate ((XII); 8.7 mmol) was dissolved in 25 mL glacial acetic acid and $NH_2OH \cdot HCl$ (9.6 mmol) and NaOAc (12 mmol) were added. The solution was stirred at room temperature for 2.5 h and then $Ac_2O$ (29 mmol) was added and the reaction stirred for 1.5 h at room temperature and at 94° C. for an additional 4 h. The excess HOAc and $Ac_2O$ were removed in vacuo. Water was added to the residue and the aq layer was neutralized with aq $NaHCO_3$. The suspension was extracted with EtOAc and the combined organic fractions were washed once with $H_2O$, and then dried over $MgSO_4$. After filtration, the filtrate was concentrated in vacuo to give an oil which solidified on standing. The cyano derivative (V) was obtained in 40% yield as a yellow solid after trituration from EtOAc/Hex: mp 169°–170° C.; $^1$H NMR ($CDCl_3$) δ8.14–8.01 (m, 2H), 7.63–7.60 (m, 1H), 7.47–7.38 (m, 1H), 7.13 (s, 1H), 5.19 (s, 1H), 4.27–4.09 (m, 2H), 3.65 (s, 3H), 2.41 (s, 3H), 1.29 (t, 3H, J=7 Hz); $^{13}$C NMR ($CDCl_3$) δ166.7, 163.7, 148.7, 146.7, 145.5, 134.3, 129.4, 123.0, 122.4, 116.5, 113.1, 111.8, 102.1, 62.0, 52.0, 39.5, 19.2, 13.9. HRMS Calcd. for $C_{18}H_{18}N_3O_6$: (M+H): 372.1196. Found: 372.1207.

EXAMPLE 9

1,4-Dihydro-2,6-dimethyl-4-(3-nitrophenyl)-5-(3-methyl-1,2,4-oxadiazol-5-yl)-3-pyridinecarboxylic acid, methyl ester The starting 1,4-dihydro-2,6-dimethyl-4-(3-nitrophenyl)-3,5-pyridinedicarboxylic acid, mono-methyl ester (XIV)[14] (11.1 mmol) was treated with carbonyl diimidazole (12 mmol) in 60 mL of MeCN. After stirring for 2 h, acetamidoxime.HCl (15.8 mmol), and $Et_3N$ (22.2 mmol) were added. The resulting mixture was refluxed for 17 h under $N_2$ and the volatiles were then removed in vacuo. The residue was taken up in $CH_2Cl_2$ and washed with $H_2O$ and brine, and dried over $MgSO_4$. After filtration, the volatiles were removed in vacuo to give a yellow foam. The crude intermediate O-acyl amidoxime was purified by flash chromatography ($SiO_2$: MeOH/EtOAc) to give 3.13 g (73%) of this intermediate. This material was then heated neat in a 200° C. oil bath for 20 min under a $N_2$ flow. The resulting dark residue was recrystallized from EtOAc/Hex to give the oxadiazole intermediate (V) in 37% yield as a yellow crystalline solid: mp 221°–222° C.; $^1$H NMR (DMSO-$d_6$) δ9.37 (s, 1H), 7.99 (m, 2H), 7.66 (m, 1H), 7.54 (t, 1H, J=7.9 Hz), 5.18 (s, 1H), 3.57 (s, 3H), 2.41 (s, 3H), 2.31 (s, 3H), and 2.23 (s, 3H); $^{13}$C NMR (DMSO-$d_6$) δ175.5, 166.9, 166.5, 149.0, 148.0, 146.6, 144.4, 134.1, 130.0, 121.7, 100.7, 95.6, 51.1, 39.4, 18.5, 18.3, and 11.4. Anal. Calcd for $C_{18}H_{18}N_4O_5$: C, 58.37; H, 4.90; N, 15.13. Found: C, 58.56; H, 4.88; N, 14.88.

3. Aniline Intermediates of Formula (IV)

EXAMPLE 10

General Reductive Procedures for the Conversion of the Nitroaryl Dihydropyridines (V) to the Anilines (IV)

Catalytic Hydrogenation Method A. To a $N_2$ solution of the nitro aromatic dihydropyridine (V) (10 mmol) in 80 mL of EtOH, was added 0.5–1.0 g of 5% Pt on sulfided carbon and the resulting suspension shaken on a Parr Hydrogenation apparatus at room temperature under 60 psi of $H_2$. After several h the reduction was usually complete as judged by theoretical $H_2$ consumption. The suspension was then filtered through Celite and the filtrate concentrated in vacuo to give the anilines (IV). These were then purified by recrystallization or flash chromatography in the indicated solvents. In some of the examples the crude aniline derivatives were converted to a salt form and then recrystallized.

Iron Method B.[15] In a 250-mL three-necked flask equipped with mechanical stirrer and reflux condenser was added a solution of $NH_4Cl$ (64 mmol) in 50 mL of $H_2O$, iron powder (38 mg-atom, 325 mesh) and a solution of the nitro aromatic dihydropyridine (V) (11 mmol) in 50 mL of MeOH. The resulting mixture was stirred at reflux for 6 h and then filtered through Celite and rinsed with copious amounts of MeOH. The filtrate was partially concentrated in vacuo to yield an aq suspension, which was extracted with $CH_2Cl_2$. The combined organic extracts were dried over $Na_2SO_4$, filtered, and the volatiles removed in vacuo to yield the crude anilines (IV). These were purified as above in the hydrogenation method.

Nickel/Borohydride Resin Method C. According to the general method of Yoon[9] the borohydride exchange resin (12 g) was suspended in 40 mL of MeOH and $Ni(OAc)_2 \cdot 4H_2O$ (0.60 mmol) was added. After stirring several min, the requisite nitro aromatic derivative (V) (6 mmol) was added and the resulting black mixture stirred overnight at room temperature. After filtration through a plug of Celite, the reaction solution was concentrated in vacuo to give the reduced aniline derivatives (IV).

EXAMPLE 11

4-(3-Aminophenyl)-1,4-dihydro-2-methyl-6-propyl-3,5-pyridinedicarboxylic acid, ethyl[5] methyl[3] ester, fumaric acid salt This compound was obtained as an orange-brown solid in 91% yield (Method B): mp 92°–95° C.; $^1$H NMR (MeOD) δ7.30–7.17 (m, 3H), 7.02–6.99 (m, 1H), 6.26 (s, 2H), 4.90 (s, 1H), 4.06 (q, 2H, J=14 Hz), 3.61 (s, 3H), 2.78–2.52 (m, 2H), 2.30 (s, 3H), 1.69–1.55 (m, 2H), 1.21 (t, 3H, J=7 Hz), 0.97 (t, 3H, J=7.4 Hz); $^{13}$C NMR (MeOD) δ170.5, 169.9, 169.04, 151.9, 147.0, 135.0, 134.9, 130.5, 127.5, 122.0, 120.3, 103.2, 103.0, 60.9, 51.4, 40.8, 34.7, 23.4, 18.6, 14.7, 14.3. Anal. Calcd. for $C_{20}H_{26}N_2O_4 \cdot 1.0C_4H_4O_4 \cdot 1.0H_2O$: C, 58.53; H, 6.55; N, 5.69. Found: C, 58.86; H, 6.22; N, 5.68.

EXAMPLE 12

4-(3-Aminophenyl)-1,4-dihydro-2,6-dimethyl-3,5-pyridine-dicarboxylic acid, ethyl methyl ester This compound was obtained in 92% yield as a grey solid after crystallization from EtOAc/Hex (Method A): mp 173°–175° C.

EXAMPLE 13

4-(3-Aminophenyl)-1,4-dihydro-2,6-dimethyl-3,5-pyridine-dicarboxylic acid, diethyl ester hydrochloride salt The compound was isolated in 82% yield (Method A) after purification by flash chromatography ($SiO_2$: EtOAc/Hex). A small portion of the aniline was converted to the HCl salt by treatment with ethereal HCl. After trituration from $Et_2O$, the compound was obtained as a pale yellow solid: mp 212°–213° C.

EXAMPLE 14

4-(3-Aminophenyl)-1,4-dihydro-2,6-dimethyl-3,5-pyridine-dicarboxylic acid, dimethyl ester The compound was obtained in 58% yield as a colorless solid after crystallization from EtOH (Method A): mp 214°–215° C.

EXAMPLE 15

4-(3-Aminophenyl)-1,4-dihydro-2,6-dimethyl-3,5-pyridine-dicarboxylic acid, n-butyl methyl ester hydrochloride salt The compound was isolated as a yellow oil in 68% yield (Method A) after flash chromatography ($SiO_2$: EtOAc/Hex). A small portion of the oil was converted to the HCl salt by treatment with ethereal HCl: mp 135°–145° C.; $^1$H NMR (DMSO-$d_6$) δ10.20 (br s, 2H), 9.12 (s, 1H), 7.29 (t, 1H, J=7.8 Hz), 7.12 (m, 3H), 4.89 (s, 1H), 3.94 (m, 2H), 3.54 (s, 3H), 2.27 (s, 3H), 2.26 (s, 3H), 1.49 (m, 2H), 1.22 (m, 2H), and 0.89 (t, 3H, J=8.0 Hz); $^{13}$C NMR (DMSO-$d_6$) δ167.2, 166.8, 149.7, 146.1, 132.1, 129.1, 125.4, 121.7, 120.6, 101.1, 101,0, 62.9, 50.7, 38.6, 30.3, 18.7, 18.3, and 15.6.

EXAMPLE 16

4-(3-Aminophenyl)-1,4-dihydro-2,6-dimethyl-3,5-pyridine-dicarboxylic acid, 1,1-dimethylethyl methyl ester The aniline was obtained in 87% yield as a yellow solid after purification by flash chromatography ($SiO_2$: EtOAc/Hex): mp 85°–90° C.; $^1$H NMR ($CDCl_3$) δ6.97 (t, 1H, J=7.7 Hz), 6.66 (d, 1H, J=7.7 Hz), 6.58 (s, 1H), 6.44 (d, 1H, J=7.8 Hz), 5.53 (br s, 1H), 4.86 (s, 1H), 3.62 (s, 3H), 3.50 (br s, 2H), 2.29 (s, 3H), 2.26 (s, 3H), and 1.39 (s, 9H); $^{13}$C NMR ($CDCl_3$) δ168.2, 167.1, 148.7, 145.9, 144.1, 142.5, 128.6, 118.5, 114.9, 113.1, 103.4, 79.8, 50.9, 39.6, 28.3, 19.7, and 19.6. Anal Calcd for $C_{20}H_{26}N_2O_4$: C, 67.02; H, 7.32; N, 7.82. Found: C, 66.97; H, 7.43; N, 7.68.

EXAMPLE 17

4-(3-Aminophenyl)-1,4-dihydro-2-cyano-6-methyl-3,5-pyridine-dicarboxylic acid, ethyl[3] methyl[5] ester This material was prepared using the general Fe/$NH_4Cl$ procedure described above for anilines (Method B). Aniline (IV) was obtained in 69% yield as a yellow solid: mp 181°–182° C.; $^1$H NMR ($CDCl_3$) δ8.73 (s, 1H), 6.96 (t, 1H, J=8 Hz), 6.60–6.44 (m, 3H), 4.92 (s, 1H), 4.25–4.08 (m, 2H), 3.70 (s, 1H), 3.58 (s, 3H), 2.30 (s, 3H), 1.23 (t, 3H, J=7 Hz); $^{13}$C NMR ($CDCl_3$) δ167.5, 164.5, 146.4, 145.6, 129.2, 118.3, 117.7, 116.6, 114.7, 114.5, 114.0, 113.8, 101.8, 61.3, 51.2, 39.1, 18.7, 14.0. Anal. Calcd. for $C_{18}H_{19}N_3O_4$: C, 61.94; H, 5.47; N, 11.53. Found: C, 61.51; H, 5.34; N, 11.75.

EXAMPLE 18

1,4-(3-Aminophenyl)-1,4-dihydro-2,6-dimethyl-5-(3-methyl-1,2,4-oxadiazol-5-yl)-3-pyridinecarboxylic acid, methyl ester This compound was prepared using the iron procedure (Method B). The aniline derivative was obtained in quantitative yield as a yellow solid: mp 248°–249° C.; $^1$H NMR (DMSO-$d_6$) δ9.08 (s, 1H), 6.80 (t, 1H, J=7.7 Hz), 6.39 (s, 1H), 6.34 (d, 1H, J=7.7 Hz), 6.27 (d, 1H, J=7.7 Hz), 4.93 (s, 1H), 4.88 (br s, 2H), 3.58 (s, 3H), 2.38 (s, 3H), 2.25 (s, 3H), and 2.23 (s, 3H); $^{13}$C NMR (DMSO-$d_6$) δ175.9, 167.2, 166.2, 148.4, 147.4, 144.9, 143.3, 128.5, 114.7, 112.7, 112.0, 101.5, 96.0, 50.7, 39.0, 18.2, and 11.2. HRMS. Calcd for $C_{18}H_{21}N_4O_3$ (M+H): 341.1614. Found: 341.1606.

EXAMPLE 19

4-(3-Aminophenyl)-5-cyano-1,4-dihydro-2,6-dimethyl-3-pyridinecarboxylic acid, methyl ester This compound was prepared using the iron procedure (Method B). The aniline was obtained in 10% yield as a tan solid after recrystallization from EtOH: mp 234°–235° C.; $^1$H NMR (DMSO-$d_6$) δ9.09 (br s, 1H), 6.90 (t, 1H, J=7.5 Hz), 6.36 (m, 2H), 6.30 (d, 1H, J=7.5 Hz), 5.01 (br s, 2H), 4.27 (s, 1H), 3.48 (s, 3H), 2.24 (s, 3H), and 1.99 (s, 3H); $^{13}$C NMR (DMSO-$d_6$) δ167.2, 148.7, 146.8, 146.0, 145.2, 128.9, 120.2, 114.6, 112.5, 99.7, 84.5, 50.7, 40.6, 18.4, and 17.5. Anal. Calcd for $C_{16}H_{17}N_3O_2 \cdot 0.22H_2O$: C, 66.91; H, 6.12; N, 14.63. Found: C, 66.91; H, 6.07; N, 14.40.

EXAMPLE 20

4-(3-Amino-4-chlorophenyl-1,4-dihydro-2,6-dimethyl-3,5-pyridinedicarboxylic acid ethyl methyl ester This dihydropyridine was obtained using the iron reduction procedure (Method B). It was isolated in 99% yield as light yellow solid: mp 68°–90° C.; $^1$H NMR (CDCl$_3$) δ7.03 (d, 1H), 6.62 (m, 2H), 5.68 (br s, 1H), 4.88 (s, 1H), 4.08 (m, 2H), 3.89 (br s, 2H), 3.63 (s, 3H), 2.29 (s, 6H), and 1.21 (t, 3H). Anal. Calcd. for $C_{18}H_{21}N_2O_4Cl$: C, 59.26; H, 5.80; N, 7.68. Found: C, 59.04; H, 5.79; N, 7.56.

EXAMPLE 21

4-[3-Amino-4-(2-propenyloxyphenyl]-1,4-dihydro-2,6-dimethyl-3,5-pyridinedicarboxylic acid dimethyl ester To a suspension of hexane-washed NaH (17 mmol, 60% in mineral oil) in 5 mL of DMF was added a solution of compound (V), $R^5$=OH (14.1 mmol) in 50 mL of DMF. The resulting dark red solution was stirred at room temperature for 10 min and then allyl bromide (22 mmol) was introduced. After the reaction was stirred an additional 21 h, it was poured into 300 mL of H$_2$O and extracted with CH$_2$Cl$_2$. The combined organic portions were washed with H$_2$O and brine and then dried over MgSO$_4$. Filtration and removal of the volatiles in vacuo afforded compound [(V), R=allyloxy] as an oil which was used without further purification and was subsequently subjected to the iron reduction method (Method B). The resulting aniline compound [(IV), R-allyloxy] was obtained in 50% yield after purification by flash chromatography (SiO$_2$: EtOAc/Hex) and was isolated as a pale yellow solid: 155°–157° C.; $^1$H NMR (DMSO-$d_6$) δ8.74 (br s, 1H), 6.58 (d, 1H, J=8.3 Hz), 6.44 (d, 1H, J=2.1 Hz), 6.26 (d of d, 1H, J's=8.3 and 2.1 Hz), 6.01 (m, 1H), 5.40 (d, 1H), 5.19 (d, 1H), 4.74 (s, 1H). 4.55 (br s, 2H), 4.32 (m, 2H), 3.54 (s, 6H), and 2.22 (s, 6H); $^{13}$C NMR (DMSO-$d_6$) δ167.7, 145.0, 143.7, 140.6, 137.2, 134.4, 116.7, 114.7, 113.2, 111.7, 101.8, 68.5, 50.6, 37.6, and 18.2. Anal. Calcd for $C_{20}H_{24}N_2O_5$: C, 64.50; H, 6.50; N, 7.52. Found: C, 64.32; H, 6.59; N, 7.35.

4. Intermediates of Formula (III)

EXAMPLE 22

General Procedure for Preparation of Formula (III) Anilide Intermediates

To a solution of an appropriate Formula (IV) aniline intermediate (2.5 mmole) in THF (50 mL) at 0° is added a chloroalkylacyl chloride (2.5 mmole) also in THF (15 mL). The reaction is stirred at 0° for 0.5 to 1 hour and then at room temperature for 0.5 to 1 hour until judged complete. Volatiles are removed in vacuo and the residue is purified, generally by flash silica gel chromatography.

EXAMPLE 23

1,4-Dihydro-4-[3-[[3-chloro-1-oxo-1-propyl]amino] phenyl]-2,6-dimethyl-3,5-pyridinedicarboxylic acid, dimethyl ester 4-(3-Aminophenyl)-1,4-dihydro-2,6-dimethyl-3,5-pyridinedicarboxylic acid, dimethyl ester (0.8 g, 2.53 mmol) was dissolved in THF (50 mL) and cooled to 0° C. 3-Chloropropionyl chloride (0.32 g, 2.53 mmol) was dissolved in THF (15 mL) and added dropwise to the mixture over 10 min. The mixture was stirred at 0° C. for 1 h., concentrated in vacuo, and the residue extracted with CH$_2$Cl$_2$/brine. The CH$_2$Cl$_2$ layer was dried over Na$_2$SO$_4$; filtered, and concentrated in vacuo. Silica gel chromatography (1:1 to 1:0 EtOAc:hexane gradient) gave the title compound (1.05 g, 100%) as a pale yellow foam.

EXAMPLE 24

1,4-Dihydro-4-[3-[[4-chloro-1-oxo-1-butyl]amino] phenyl]-2,6 dimethyl-3,5-pyridinedicarboxylic acid ester 4-(3-Aminophenyl)-1,4-dihydro-2,6-dimethyl-3,5-pyridine-dicarboxylic acid, dimethyl ester (1.0 g, 3.16 mmol) was dissolved in THF (50 mL) and cooled to 0° C. 4-Chlorobutyryl chloride (0.446 g, 3.16 mmol) was dissolved in THF (10 mL) and added dropwise to the mixture over 5 min. The mixture was stirred at 0° C. for 0.5 h. and then at 23° C. for 1 h. The solvent was removed in vacuo and the concentrate chromatographed over silica gel (1:4 to 1:0 EtOAc:hexane gradient) to give the title compound (1.33 g, 100%) as a pale yellow foam.

EXAMPLE 25

1,4-Dihydro-4-[3-[[5-chloro-1-oxo-1-pentyl]amino] phenyl]-2,6-dimethyl-3,5-pyridinedicarboxylic acid, dimethyl ester 4-(3-Aminophenyl)-1,4-dihydro-2,6-dimethyl-3,5-pyridine-dicarboxylic acid, dimethyl ester (2.3 g, 7.28 mmol) was dissolved in THF (50 mL) and cooled to 0° C. 5-Chlorovaleryl chloride (1.13 g, 7.28 mmol) was dissolved in THF (15 mL) and added dropwise to the mixture over 15 min. The mixture was stirred at 0° C. for 1 h., the solvent removed in vacuo, and the residue was extracted using CH$_2$Cl$_2$/water. The CH$_2$Cl$_2$ layer was dried over Na$_2$SO$_4$, filtered, and concentrated in vacuo. Silica gel chromatography (1:1 to 1:0 EtOAc:hexane gradient) of the concentrate gave the title compound (3.16 g, 100%) as a pale yellow foam.

5. Intermediates of Formula II

EXAMPLE 26

General Chloroalkyl Isocyanate Procedure for Preparation of Formula II Urea Intermediates To a solution of the appropriate Formula (IV) aniline intermediate (6 mmol) in CH$_2$Cl$_2$ (30 mL) under N$_2$ is added the chloroalkyl isocyanate (7 mmol). The reaction is stirred at room temperature or at reflux until judged complete by TLC analysis (2–24 h). The reaction solution is washed with H$_2$O and brine and then dried (MgSO$_4$). After filtration, the volatiles are removed in vacuo and the residue is generally taken up in MeCN (35 mL) and immediately carried on with reaction with a selected piperidine or tetrahydropyridine reactant of Formula (X).

EXAMPLE 27

Preparation of Formula XXXIV) isocyanate Intermediates a) 1,4-Dihydro-4-[3-[(methoxycarbonyl)amino]phenyl]-2,6-dimethyl-3,5-pyridinedicarboxylic acid, dimethyl ester (XXIV). A solution of 1,4-dihydro-4-(3-aminophenyl)-2,6-dimethyl-3,5-pyridinedicarboxylic acid, dimethyl ester (IV: 63.2 g, 200 mmol) and pyridine (18 mL, 220 mmol) in $CH_2Cl_2$:MeCN 1:1 (1.5 L) was cooled to 0° C. A solution of methyl chloroformate (16 mL, 210 mmol) in $CH_2Cl_2$ (50 mL) was added dropwise over 10 min. Stirring was continued at 0° C. for 30 min, then the reaction was warmed to room temperature and stirred for an additional hour. The reaction mixture was washed with saturated $Na_2CO_3$ (500 mL) and rinsed with $H_2O$ (2×500 mL). The organic extract was filtered to afford a white solid (37.1 g). The filtrate was then dried ($Na_2SO_4$), and the solvent was removed in vacuo. The residue was suspended in a minimum of EtOAc and filtered. The resulting solid was rinsed with a small amount of EtOAc, followed by $Et_2O$ to give an additional 30.8 g. Both crops were combined for a yield of 67.9 g (91%): mp 215°–218° C.; $^1H$ NMR (DMSO-$d_6$) δ9.51 (s, 1H), 8.88 (s, 1H), 7.28 (s, 1H), 7.22 (d, 1H, J=8.1 Hz), 7.08 (t, 1H, J=7.8 Hz), 6.74 (d, 1H, J=7.8 Hz), 4.85 (s, 1H), 3.62 (s, 3H), 3.54 (s, 6H), 2.24 (s, 6H); $^{13}C$ NMR (DMSO-$d_6$) δ167.4, 153.9, 148.2, 145.8, 138.9, 128.3, 121.0, 117.1, 115.9, 101.3, 51.5, 50.6, 38.4, 18.2; Anal Calcd for $C_{19}H_{22}N_2O_6 \cdot 0.1\ H_2O$: C, 60.66; H, 5.95; N, 7.45. Found: C, 60.50; H, 5.85; N, 7.55.

b) 1,4-Dihydro-4-(3-isocyanatophenyl)-2,6-dimethyl-3,5-pyridinedicarboxylic acid, dimethyl ester (XXXIV). According to the procedure described by Valli and Alper,[16] a solution of the carbamate (XXIV) (15.2 g, 40.6 mmol) and $Et_3N$ (8.4 mL, 60 mmol) in anhydrous THF (300 mL) was refluxed under $N_2$ for 5 min, and then allowed to cool for 10 min. B-Chlorocatecholborane (8.78 g, 57 mmol) was added, and the resulting mixture was refluxed under $N_2$ for 5 min. The solvent was then removed in vacuo, and the residue was taken up in $CH_2Cl_2$ (300 mL). The resulting solution was washed with 1N aqueous HCl (150 mL), followed by 1N aqueous NaOH (150 mL). The organic extract was dried ($Na_2SO_4$) and the solvent was removed in vacuo to furnish a cream solid (13.9 g, quantitative yield): mp 170°–173° C.; $^1H$ NMR (CDCl$_3$) δ7.11 (m, 2H), 6.96 (s, 1H), 6.86 (d, 1H, J=7.5 Hz), 5.74 (s, 1H), 4.97 (s, 1H), 3.65 (s, 6H), 2.34 (s, 6H); $^{13}C$ NMR (CDCl$_3$) δ167.8, 149.2, 144.4, 133.0, 129.0, 125.3, 124.0, 122.7, 103.5, 51.1, 39.3, 19.6; IR (KBr): 2272 cm$^{-1}$; Anal Calcd for $C_{18}H_{18}N_2O_5$: C, 63.15; H, 5.30; N, 8.18. Found: C, 63.17; H, 5.33; N, 7.98.

6. Intermediates of Formula XIX and XX

EXAMPLE 28

4(3-Methoxyphenyl)piperidine-1-propanenitrile (XIX)

A solution of 4-(3-methoxyphenyl)piperidine[17] (Xa, 26.2 g, 137 mmol) and acrylonitrile (10.8 mL, 164 mmol) in MeCN (150 mL) was refluxed for 4 h, and then the solvent was removed in vacuo. An amber oil was obtained, which underwent a rapid, exothermic crystallization to form a white solid (32.3 g, 96% yield): mp 90°–94° C.; $^1H$ NMR (CDCl$_3$) δ7.22 (t, 1H, J=7.5 Hz), 6.81 (d, 1H, J=8.1 Hz), 6.76 (m, 2H), 3.80 (s, 3H), 3.01 (d, 2H, J=11.7 Hz), 2.72 (t, 2H, J=6.9 Hz), 2.54 (t, 2H, J=7.2 Hz), 2.46 (m, 1H), 2.19 (t, 2H, J=11.1 Hz), 1.77 (m, 4H); $^{13}C$ NMR (CDCl$_3$) δ159.7, 147.7, 129.4, 119.2, 118.9, 112.7, 111.4, 55.1, 53.8, 42.4, 33.2, 15.9; IR (KBr): 2246 cm$^{-1}$; Anal Calcd for $C_{15}H_{20}N_2O \cdot 0.2\ H_2O$: C, 72.66; H, 8.29; N, 11.30. Found: C, 72.83; H, 8.18; N, 11.19.

EXAMPLE 29

4-(3-Methoxyphenyl)piperidine-1-propanamine (XX)

A solution of Example 28 product (31.26 g, 128 mmol) in MeOH (850 mL) and 30% aqueous $NH_3$ (150 mL) containing Raney nickel was hydrogenated for 1 h at 50 psi in a Parr apparatus. The catalyst was removed by filtration over Celite, and the solvent was removed in vacuo from the filtrate. The residue was taken up in $CH_2Cl_2$, dried ($Na_2SO_4$), and the solvent was removed in vacuo to afford a light amber oil (31.08 g, 98% yield): $^1H$ NMR (CDCl$_3$) δ7.16 (t, 1H, J=7.5 Hz), 6.77 (d, 1H, J=7.5 Hz), 6.74 (s, 1H), 6.69 (d, 1H, J=7.5 Hz), 3.74 (s, 3H), 3.01 (d, 2H, J=11.4 Hz), 2.71 (t, 2H, J=6.9 Hz), 2.44 (m, 1H), 2.38 (t, 2H, J=7.2 Hz), 1.97 (t, 2H, J=11.4 Hz), 1.78 (m, 4H), 1.63 (m, 4H); $^{13}C$ NMR (CDCl$_3$) δ159.6, 148.1, 129.3, 119.3, 112.6, 111.3, 56.9, 55.1, 54.5, 42.8, 40.9, 33.4, 30.8; Anal Calcd for $C_{15}H_{24}N_2O \cdot 0.4\ H_2O$: C, 70.50; H, 9.78; N, 10.96. Found: C, 70.48; H, 9.66; N, 10.92.

7. Intermediates of Formula (X)

Many of the piperidine and tetrahydropyridine intermediates of Formula (X) are known;[12, 17, 18] and several are commercially available. The following examples are intended to illustrate typical syntheses of various Formula (X) compounds.

EXAMPLE 30

General Preparation of Intermediate Piperidinols (XV)

The appropriate arylbromide (55 mmol) dissolved in anhydrous tetrahydrofuran (60 mL) was stirred at –78° C. for 15 minutes. The nBuLi (55 mmol) was then added over a period of 20 minutes. This mixture was stirred for 15 minutes. N-Benzyl-4-piperidone (XVIa) or N-t-butyloxycarboxyl-4-piperidone (XVIb) (39 mmol) was then added in anhydrous tetrahydrofuran (10 mL) at –78° C. over 20 minutes. The reaction was stirred for 30 minutes at –78° C. and quenched cold over saturated ammonium chloride (80 mL). The aqueous layer was extracted with methylene chloride, dried over magnesium sulfate, and concentrated in vacuo. The products were purified by flash chromatography 30:1 methylene chloride/acetone and used directly in the next reaction. The intermediates were generally used immediately, however, the benzylpiperidinol of Example 31 was isolated and characterized.

EXAMPLE 31

1-Benzyl-4-(3-methoxyphenyl)-4-piperidinol, fumarate salt

This intermediate was obtained as a white solid in 60% yield: mp 112°–115° C; $^1H$-NMR (DMSO-$d_6$) δ7.31 (m, 6H), 7.02 (m, 2H), 6.76 (m, 1H), 6.56 (s, 2H), 3.75 (s, 2H), 3.72 (s, 3H), 2.78 (m, 2H), 2.65 (m, 3H), 2.04 (m, 2H), 1.59 (m, 2H); $^{13}C$ NMR (DMSO-$d_6$) δ167.18, 159.07, 151.31, 136.13, 134.68, 129.66, 128.93, 128.29, 127.55, 116.98, 111.60, 110.77, 69.23, 61.18, 54.92, 48.48, 36.99; Anal. Calcd. for $C_{19}H_{23}NO_2 \cdot 0.7\ C_4H_4O_4$: C, 69.15; H, 6.87; N, 3.70. Found: C, 69.43; H, 6.78; N, 3.91.

EXAMPLE 32

Preparation of Compounds of Formula Xa

The requisite alcohol intermediate (XVa) (14 mmol) was refluxed overnight with p-toluene sulfonic acid (20 mmol) in toluene (20 mL). The toluene was concentrated off to leave an oil which was triturated in ether/hexane to give a solid. The solid (14 mmol) was dissolved in ethanol (20 mL) and hydrogenated at 50 psi with Pearlman's catalyst (20% by weight). The reaction required 4 to 6 hours for completion.

The crude heterogeneous reaction mixture was then filtered through a plug of celite with several rinsings of ethanol. The products of Formula (Xa) were obtained as oils after concentration in vacuo. A small portion of the intermediate piperidines were generally converted to their fumaric acid salt for characterization.

EXAMPLE 33

4-[(3-Phenyl)phenyl]piperidine

This compound was obtained as an oil in 28% yield. $^1$H NMR (CDCl$_3$) δ7.32 (m, 9H), 3.27 (m, 2H), 2.88 (m, 3H), 1.79 (m, 4H); HRMS Calcd. for C$_{17}$H$_{20}$N (M+H) 238.1596. Found: 238.1590.

EXAMPLE 34

4-[3-(2-Propynyloxy)phenyl]piperidine (Xa)

a) 1-Acetyl-4-(3-hydroxyphenyl)piperidine. Ac$_2$O (9.00 g, 88.2 mmol) was added to a solution of 4-(3-methoxyphenyl)piperidine (14.4 g, 75.4 mmol) and Et$_3$N (10.5 g, 104 mmol) in CH$_2$Cl$_2$ (200 mL). After stirring overnight (18 h), it was washed with H$_2$O, brine and then dried over MgSO$_4$. Filtration and concentration in vacuo yielded 17.1 g of the intermediate acetamide. This material was taken up in CH$_2$Cl$_2$ (200 mL) and cooled to −78° C. in a cold bath (i-PrOH-CO$_2$), and then BBr$_3$ (135 mL, 135 mmol, 1.0M in CH$_2$Cl$_2$) was slowly added via addition funnel. After the addition was complete the cold bath was removed and the suspension was allowed to warm to room temperature and mechanically stir overnight (16 h). Water (200 mL) was then carefully added and the mixture extracted with CH$_2$Cl$_2$. The combined organic portions were washed with H$_2$O, brine, and dried over MgSO$_4$. After filtration, the volatiles were removed in vacuo to furnish a yellow solid. Recrystallization from i-PrOH gave 11.6 g (52.9 mmol, 70% yield) of the subject intermediate as a colorless white solid: mp 144°–145° C.; $^1$H NMR (DMSO-d$_6$) δ9.28 (s, 1H), 7.07 (t, 1H, J=7.6 Hz), 6.58 (m, 3H), 4.50 (d, 1H, J=13.0 Hz), 3.88 (d, 1H, J=13.0 Hz), 3.08 (t, 1H, J=12.7 Hz), 2.61 (m, 2H), 2.02 (s, 3H), 1.74 (m, 2H), 1.44 (m, 1H), and 1.33 (m, 1H); $^{13}$C NMR (DMSO-d$_6$) δ157.7, 157.2, 147.0, 129.1, 117.1, 113.4, 112.9, 46.1, 41.5, 41.2, 33.1, 32.5, and 21.2. Anal. Calcd. for C$_{13}$H$_{17}$NO$_2$: C, 71.21; H, 7.81; N, 6.39. Found: C, 71.14; H, 7.68; N, 6.37.

b) 4-[3-(2-Propynyloxy)phenyl]piperidine. A mixture of the N-acetyl-3-hydroxyphenylpiperidine (6.73 g, 30.7 mmol), propargyl bromide (7.70 g, 51.8 mmol, 80% in toluene), K$_2$CO$_3$ (4.61 g, 33.4 mmol) and acetone (160 mL) was refluxed under N$_2$ for 2 days. The mixture was then filtered and concentrated to give 8.25 g of the intermediate propargyl ether. This material was taken up in EtOH (80 mL) and 9N aq NaOH (30 mL) was added. After refluxing overnight (15 h) the dark solution was poured into 500 mL of water and extracted with CH$_2$Cl$_2$. The combined organic portions were washed with H$_2$O, brine, and dried over MgSO$_4$. Filtration and concentration in vacuo furnished 3.93 g (18.3 mmol, 60% yield) of (Xa) product as a yellow oil: IR (film) 2118 cm$^{-1}$; $^1$H NMR (CDCl$_3$) δ7.18 (m, 1H), 6.81 (m, 3H), 4.65 (m, 2H), 3.19 (m, 2H), 2.73 (m, 3H), 2.60 (m, 1H), 2.49 (m, 1H), 1.86 (m, 2H), and 1.64 (m, 2H); $^{13}$C NMR (CDCl$_3$) δ157.6, 148.1, 129.3, 120.0, 113.6, 112.1, 78.5, 75.3, 55.6, 46.8, 42.7, and 33.9. HRMS. Calcd for C$_{14}$H$_{18}$NO (M+H): 216.1388. Found: 216.1382.

EXAMPLE 35

Preparation of 4-Hydroxy-4-Arylpiperidines (Xb)

The alcohol intermediate (XVa) (0.9 mmol) was dissolved in ethanol (20 mL) and palladium on carbon (20% by weight) was added along with glacial acetic acid (1 mL). The reaction was hydrogenated at 50 psi for 4 hours. The crude mixture was filtered through a plug of celite and the plug was rinsed several times with ethanol. The organic layer was concentrated down to an oil. The oil was redissolved in methylene chloride and washed twice with saturated sodium bicarbonate. The organic layer was dried over magnesium sulfate and concentrated in Vacuo.

EXAMPLE 36

4-(3-Methoxyphenyl)-4-piperidinol, fumarate salt

This intermediate was obtained as an off white solid in 99% yield: mp 141°–145° C; $^1$H NMR (DMSO-d$_6$) δ7.25 (t, 1H, J=8Hz), 7.01 (m, 2H), 6.80 (dd, 1H, J=8 Hz), 6.51 (s, 2H), 3.73 (s, 4H), 3.15 (m, 5H), 2.15 (m, 2H), 1.68 (m, 2H); $^{13}$C NMR (DMSO-d$_6$) δ167.7, 159.2, 150.3, 134.9, 129.2, 116.7, 111.9, 110.7, 68.5, 54.9, 34.5; HRMS Calcd. for C$_{12}$H$_{18}$NO$_2$ (M+H) 208.1337. Found: 208.1335.

EXAMPLE 37

Preparation of Tetrahydropyridines (Xc)

The alcohol intermediate (XVb) (5.4 mmol) was stirred in methylene chloride (10 mL) and trifluoroacetic acid (54 mmol) was added. The reaction was refluxed for 6 hours. The crude reaction mixture was quenched over 10% aqueous sodium carbonate. The aqueous layer was extracted several times with methylene chloride, dried over magnesium sulfate, and concentrated in vacuo.

EXAMPLE 38

1,2,3,6-Tetrahydro-4-[3-(2-propenyloxy)phenyl]pyridine fumaric acid salt

This compound was obtained as an orange oil in 90% yield; mp 154°–157° C; $^1$H NMR (CDCl$_3$) δ7.21 (m, 2H), 6.92 (m, 2H), 6.78 (m, 1H), 6.02 (m, 1H), 5.32 (m, 2H), 4.51 (m, 2H), 3.63 (br s, 2H), 3.18 (m, 2H), 2.56 (br s, 2H); HRMS Calcd. for C$_{14}$H$_{18}$NO (M+H) 216.1388. Found: 216.1385.

EXAMPLE 39

4-(2-Phenoxyphenyl)-4-piperidinol (Xb)

a) 1-Bromo-2-phenoxybenzene. This compound was prepared according to the procedure described by Williams.[12] Phenol (9.4 g, 100 mmol) was added to a suspension of NaOMe (5.3 g, 98 mmol) in anhydrous benzene (100 mL), and the resulting solution was distilled to dryness. The residue was cooled, anhydrous pyridine (150 mL) was added, and the solution heated to reflux under N$_2$. Dibromobenzene (50 g, 210 mmol) was then added, followed by CuCl (1.5 g), and the mixture was refluxed for 2 days. After cooling, the reaction mixture was partitioned between H$_2$O (100 mL) and Et$_2$O (200 mL). The organic extract was acidified with conc. HCl in ice, and was further rinsed with 1N HCl (100 mL), H$_2$O (2×100 mL) and brine (100 mL). The organic extract was dried over Na$_2$SO$_4$, and the solvent removed in vacuo. The residue was taken up in CH$_2$Cl$_2$ and filtered through silica gel, and the solvent was removed from the filtrate in vacuo. Distillation of the residue via a Kugelrohr apparatus gave product as a colorless oil (11.5 g, 46% yield):[19] $^1$H NMR (CDCl$_3$) δ7.62 (d, 1H, J=7.8 Hz), 7.30 (t, 2H, J=8.4 Hz), 7.24 (t, 1H, J=7.5 Hz), 7.10 (t, 1H, J=7.2 Hz), 7.02 (d, 1H, J=7.8 Hz), 6.96 (m, 3H); $^{13}$C NMR (CDCl$_3$)

δ156.9, 153.7, 133.8, 129.8, 128.7, 125.0, 123.4, 120.6, 118.1, 114.9. Anal. Calcd. for $C_{12}H_9BrO\cdot0.4\ H_2O$: C, 56.23; H, 3.85. Found: C, 56.11; H, 3.54.

b) 4-(2-Phenoxyphenyl)-1-(phenylmethyl)-4-piperidinol. To a stirred solution of the 1-bromo-2-phenoxybenzene (3.0 g, 12 mmol) in anhydrous THF (20 mL) at −78° C. under $N_2$ was slowly added n-butyllithium (2.0M in pentane, 6.0 mL, 12 mmol). The resulting solution was stirred for 30 min, followed by the dropwise addition of 1-benzyl-4-piperidinone (1.9 g, 10 mmol) in anhydrous THF (10 mL). The mixture was stirred for 1 hr at −78° C., and then quenched with saturated $NH_4Cl$. Sufficient $H_2O$ was added to dissolve any solids, the layers separated, and the aqueous extract discarded. The organic extract was dried over $Na_2SO_4$, and the solvent removed in vacuo. Flash chromatography of the residue ($SiO_2$: $MeOH/CH_2Cl_2$), afforded a viscous, light yellow oil (2.46 g, 71% yield): $^1H$ NMR ($CDCl_3$) δ7.33 (m, 11H), 7.03 (d, 2H, J=7.5 Hz), 6.76 (d, 1H, J=8.1 Hz), 3.56 (s, 2H), 3.52 (s, 1H), 2.75 (m, 2H), 2.56 (t, 2H, J=11.7 Hz), 2.22 (t, 2H, J=12.6 Hz), 2.04 (m, 2H); $^{13}C$ NMR ($CDCl_3$) δ156.2, 155.8, 138.6, 137.4, 130.0, 129.3, 128.3, 128.2, 126.9, 126.2, 124.1, 123.3, 119.7, 118.7, 71.1, 63.2, 49.2, 36.4. Anal. Calcd. for $C_{24}H_{25}NO_2\cdot0.7\ H_2O$: C, 77.47; H, 7.15; N, 3.77. Found: C, 77.35; H, 6.90; N, 4.13.

c) 4-(2-Phenoxyphenyl)-4-piperidinol. A solution of the product from b) (1.0 g, 2.9 mmol) in absolute EtOH (30 mL) containing AcOH (9 mL) and 10% Pd/C (200 mg) was shaken on a Parr apparatus overnight under $H_2$ (50 psi). The catalyst was removed by filtration over Celite, and the filtrate was concentrated in vacuo to yield a white solid. This solid was triturated in EtOAc and collected by filtration to give a white solid (490 mg, 66% yield): mp=150°–152° C.; $^1H$ NMR (DMSO-$d_6$) δ7.73 (d, 1H, J=7.8 Hz), 7.36 (t, 2H, J=8.1 Hz), 7.17 (t, 1H, J=7.5 Hz), 7.09 (t, 2H, J=7.5 Hz), 6.94 (d, 2H, J=8.1 Hz), 6.69 (d, 1H, J=7.8 Hz), 4.81 (s, 1H), 2.92 (t, 2H, J=10.5 Hz), 2.62 (d, 2H, J=9.0 Hz), 2.26 (t, 2H, J=12.6 Hz), 1.40 (d, 2H, J=12.6 Hz); $^{13}C$ NMR (DMSO-$d_6$) δ157.3, 153.6, 140.4, 130.0, 127.9, 127.5, 123.2, 123.0, 119.6, 118.6, 70.7, 41.8, 36.3. Anal. Calcd. for $C_{17}H_{19}NO_2\cdot0.1\ CH_2Cl_2$: C, 73.93; H, 6.97; N, 5.04. Found: C, 74.04; H, 6.63; N, 4.96.

B. SYNTHESIS OF FORMULA I PRODUCTS

1. B is a Covalent Bond

EXAMPLE 40

1,4-Dihydro-4-[3-[[3-(4-phenylpiperidin-1-yl)-1-oxo-1-propyl]amino]phenyl]-2,6-dimethyl-3,5-piperidinedicarboxylic acid, dimethyl ester 1,4-Dihydro-4-[3-[[3-chloro-1-oxo-1-propyl]amino]phenyl]-1,6-dimethyl-3,5-pyridinedicarboxylic acid, dimethyl ester (1.05 g, 2.53 mmol), 4-phenylpiperidine (0.46 g, 3.1 mmol), micropulverized potassium carbonate (1.0 g, 7.2 mmol) and KI (1.0 g, 6.0 mmol) were refluxed in $CH_3CN$ (50 mL) for 24 h. The solvent was removed in vacuo and the residue extracted with $CH_2Cl_2$/brine. The $CH_2Cl_2$ layer was dried over $Na_2SO_4$ and the solvent was removed in vacuo and the concentrate chromatographed over silica gel (1:4 to 1:0 EtOAc:hexane gradient) to give the title compound (1.33 g, 100%) as a pale yellow foam.

EXAMPLE 41

1,4-Dihydro-4-[3-[[4-(4-phenylpiperidin-1-yl)-1-oxo-1-butyl]amino]phenyl]-2,6-dimethyl-3,5-pyridinedicarboxylic acid, dimethyl ester fumarate 1,4-Dihydro-4-[3-[[4-chloro-1-oxo-1-butyl]amino]phenyl]-2,6-dimethyl-3,5-pyridinedicarboxylic acid, dimethyl ester (0.69 g, 1.64 mmol), 4-phenylpiperidine (1.2 eq., 0.29 g, 1.97 mmol), micropulverized potassium carbonate (0.5 g) and KI (0.5 g) were refluxed in $CH_3CN$ (50 mL) for 48 h. The solvent was removed in vacuo and the residue was extracted using $CH_2Cl_2$/brine. The $CH_2Cl_2$ layer was dried over $Na_2SO_4$ and evaporated to give the crude product. Chromatography over silica gel (0–20% MeOH-EtOAc as eluent) gave the free base (310 mg, 35%) as a viscous oil. The purified product was dissolved in EtOAc and 2 eq. of fumaric acid dissolved in MeOH was added. Upon standing in the freezer a precipitate formed which was filtered and washed with EtOAc to yield 125 mg (33%) of the fumarate salt, mp 189°–190° C.: IR (KBr) 1694, 1590, 1558, 1490, 1436, 1216 $cm^{-1}$; $^1H$ NMR (300 MHz, DMSO-$d_6$) δ1.62–1.79 (m, 7H), 2.09 (t, J=10.2 Hz, 2H), 2.24 (s, 6H), 2.31 (t, J=7.2 Hz, 2H), 2.41 (t, J=7.2 Hz, 2H), 3.02 (d, J=11.4 Hz, 2H), 3.53 (s, 6H), 4.86 (s, 1H), 6.53 (s, 2H), 6.79 (d, J=7.8 Hz, 1H), 7.06–7.27 (m, 6H), 7.36 (s, 1H), 7.46 (d, J=8.0Hz, 1H), 8.89 (s, 1H), 9.77 (s, 1H); MS (FAB) m/e 546 ($MH^+$). Anal Calcd. for $C_{32}H_{39}N_3O_5\cdot1.0\ C_4H_4O_4\cdot0.1\ H_2O$: C, 65.16; H, 6.56; N, 6.33. Found: C, 64.81; H, 6.76; N, 6.47.

Some additional Formula I compounds, wherein B is a covalent bond, are listed in Table 1.

TABLE 1

Additional Formula I Products

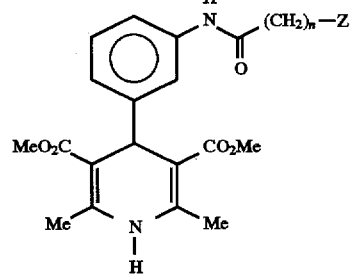

| Ex. | n | Z | mp °C. | Yield % |
|---|---|---|---|---|
| 42 | 2 | 4-Ph-piperidine | 192–93 | 86 |
| 43 | 4 | 4-Ph-piperidine | 133–35 | 67 |
| 44 | 5 | 4-Ph-piperidine | 195–97 | 39 |
| 45 | 4 | 4-OH-4-Ph-piperidine | >220 | 77 |
| 46 | 4 | 4-CN-4-Ph-piperidine | >220 | 64 |

EXAMPLE 47

Phosphate Variation-1,4-Dihydro-4-[3-[[[4-[4-(3-methoxyphenyl)-1-piperidinyl]butyl]carbonyl]amino]phenyl]-2,6-dimethyl-3,5-pyridinedicarboxylic acid dimethyl ester a) 1,4-Dihydro-4-[3-[[[(diethylphosphonate)methyl]carbonyl]amino]phenyl]-2,6-dimethyl-3,5-pyridinedicarboxylic acid, dimethyl ester (XXII). A solution of diethylphosphonoacetic acid (1.96 g, 10.0 mmol) in $CH_2Cl_2$ (30 mL) was treated sequentially with 4-dimethylaminopyridine (DMAP, 50 mg), 2-mercaptothiazoline (1.19 g, 10.0 mmol), and DCC (1.19 g, 10.0 mmol) at 25° C.[20] The reaction was stirred for 2 h followed by the addition of aniline (IV) (3.16 g, 10.0 mmol). The mixture was then stirred an additional 90 min followed by filtration through celite. The filtrate was concentrated in vacuo and the resulting residue was purified by silica gel chromatography (20:1 EtOAc/MeOH), providing pure (XXII) product (4.0 g, 80%) as a gold resin: $^1H$ NMR (CDCl$_3$) δ8.64 (s, 1H), 7.35 (s, 1H), 7.28 (d, 1H, J=7.6 Hz), 7.09 (t, 1H, J=7.6 Hz), 6.98 (d, 1H, J=7.6 Hz), 6.30 (s, 1H), 4.94 (s, 1H), 4.10 (m, 4H), 3.58 (s, 6H), 2.90 (d, 2H, J=20.7 Hz), 2.24 (s, 6H), 1.28 (t, 6H, J=7.1 Hz); $^{13}$C NMR (CDCl$_3$) δ167.9, 161.8, 148.2, 144.7, 137.5, 128.3, 123.9, 118.9, 117.8, 103.1, 62.9, 50.8, 39.0, 36.1 (d, J=129 Hz), 19.2, 16.2; IR (KBr) 3315, 2985, 1657, 1612, 1555, 1214, 1021 cm$^{-1}$; MS (ESI) 493 (M−H, 100). Anal. Calcd. for C$_{23}$H$_{31}$N$_2$O$_8$P: C, 55.87; H, 6.32; N, 5.67. Found: C, 55.51; H, 6.36; N, 5.57.

b) 1,4-Dihydro-4-[3-[[[4-[4-(3-methoxyphenyl)-1-piperidinyl]-E-but-1-ene-1-yl]carbonyl]amino]phenyl]-2,6-dimethyl-3,5-pyridinedicarboxylic acid, dimethyl ester, hydrochloride salt (XXI). Phosphonate (XXII) (988 mg, 2.00 mmol) in THF (5 mL) was treated with NaH (240 mg of a 60% suspension in mineral oil, 6.0 mmol) and stirred for 30 min. In a separate flask, acrolein (133 µL, 2.00 mmol) was added dropwise to a 0° C. solution of 4-(3-methoxyphenyl) piperidine (392 mg, 2.00 mmol), DBU (3.0 µL, 2 mmol), and THF (5.0 mL). This mixture was stirred for 20 min and then added to the above phosphonate solution. The resulting mixture was stirred for 1 h at 25° C. The reaction was then quenched with H$_2$O (10 mL) and the product extracted with a 5:1 mixture of ether/THF. The product was then concentrated in vacuo and chromatographed on silica gel (10:1 EtOAc/MeOH) to afford pure (XXI) (172 mg, 15%). The product was characterized as its HCl salt: mp 155° C.; $^1$H NMR (DMSO-d$_6$) δ10.74 (bs, 1H), 10.12 (s, 1H), 9.01 (s, 1H), 7.51 (d, 1H, J=8.1 Hz), 7.46 (s, 1H, 7.25 (t, 1H, J=8.4 Hz), 7.13 (t, 1H, J=8.1 Hz), 6.82 (m, 4H), 6.72 (dt, 1H, J=6.6, 15.4 Hz), 6.26 (d, 1H, J=15.4 Hz), 4.88 (s, 1H), 3.74 (s, 3H), 3.60 (m, 2H), 3.56 (s, 6H), 3.22 (m, 2H), 3.03 (m, 2H), 2.76 (m, 3H), 2.27 (s, 6H), 2.0 (m, 4H); $^{13}$C NMR (DMSO-d$_6$) δ167.4, 162.9, 159.3, 148.1, 145.9, 145.8, 138.8, 138.7, 129.6, 128.3, 126.9, 122.1, 118.6, 118.1, 117.1, 112.7, 111.7, 101.2, 54.9, 54.2, 51.8, 50.6, 38.7, 38.4, 29.7, 26.0, 18.2; IR (KBr) 3448, 2948, 2675, 1678, 1644, 1608, 1550, 1216 cm$^{-1}$; Anal. Calcd. for C$_{34}$H$_{41}$N$_3$O$_6$·HCl·H$_2$O: C, 63.60; H, 6.91; N, 6.54. Found: C, 63.49; H, 6.86; N, 6.35.

c) 1,4-Dihydro-4-[3-[[[4-[4-(3-methoxyphenyl)-1-piperidinyl]butyl]carbonyl]amino]phenyl]-2,6-dimethyl-3,5-pyridinedicarboxylic acid, dimethyl ester, hydrochloride salt. To a solution of amide (XXI) (200 mg, 0.34 mmol) dissolved in MeOH (2.0 mL) was added Pd on carbon (10 mg, 10% Pd). The mixture was stirred under 1 atm of H$_2$ for 12 h. The mixture was then filtered through celite and the filtrate concentrated in vacuo to provide pure Formula I product (122 mg, 60%): mp 115°−120° C.; $^1$H NMR (CDCl$_3$) δ9.16 (s, 1H), 7.59 (d, 1H, J=8.0 Hz), 7.50 (s, 1H), 7.19 (t, 1H, J=7.7 Hz), 7.08 (t, 1H, J=8.0 Hz), 6.98 (m, 2H), 6.75 (m, 3H), 4.97 (s, 1H), 3.75 (s, 3H), 3.60 (s, 6H), 3.47 (m, 2H), 2.88 (m, 2H), 2.67 (m, 3H), 2.36 (m, 4H), 2.30 (s, 6H), 1.94 (m, 2H), 1.80 (m, 2H), 1.68 (m, 2H); $^{13}$C NMR (CDCl$_3$) δ170.9, 168.2, 159.7, 148.3, 145.2, 144.5, 138.6, 138.5, 129.7, 128.0, 123.2, 118.8, 117.7, 112.8, 111.8, 102.9, 55.1, 53.0, 52.9, 50.8, 40.2, 38.9, 36.1, 29.9, 23.4, 22.5, 19.2; IR (KBr) 3320, 2947, 1684, 1607, 1548, 1489, 1434, 1214 cm$^{-1}$. HRMS. Calcd. for C$_{34}$H$_{44}$O$_6$N$_3$ (M+H): 590.3230. Found: 590.3239.

2. B is NH

EXAMPLE 48

General Procedure from Formula II Intermediates (Generated in Situ)

To a solution of the requisite aniline (IV) (6 mmol) under N$_2$ in 30 mL of CH$_2$Cl$_2$, was added 7 mmol of 3-chloropropyl isocyanate. The reaction was then stirred at room temperature or at reflux until judged complete by TLC analysis (2–24 h). The solution was washed with H$_2$O and brine and then dried over MgSO$_4$. After filtration, the volatiles were removed in vacuo and the residue was taken up in 35 mL of MeCN. To this solution was added the appropriate Formula (X) piperidine or tetrahydropyridine compound (10 mmol), micropulverized K$_2$CO$_3$ (7 mmol), and a catalytic amount of NaI (10 mg). The resulting suspension was allowed to reflux overnight under N$_2$ and then poured into 100 mL of H$_2$O. After extraction with CH$_2$Cl$_2$, the combined organic fractions were washed with H$_2$O and brine, and dried over MgSO$_4$. The suspension was filtered and the filtrate concentrated in vacuo to furnish the crude products of Formula I. These were then purified by flash chromatography (SiO$_2$: ammoniated EtOAc/MeOH) and a salt generally prepared from the free base.

There were, in general, two variations on this procedure.

Method A. The chloroalkyl dihydropyridines (II) (2.2 mmol) were alkylated as a neat melt at 134° C. with the desired Formula (X) compounds (2.2 mmol). The reaction was monitored by TLC and typically were completed in 15 minutes to an hour. The crude mixtures were purified initially by flash chromatography (SIO2:EtOAc/MeOH) followed by preparative plates (0.5 mm SiO$_2$ plates) eluted with MeOH or 10% MeOH/CH$_2$/Cl$_2$.

Method B. The chloroalkylurea dihydropyridines (II) (4.9 mmol) were alkylated with the corresponding Formula (X) compounds (4.5 mmol) using potassium carbonate (6.7 mmol) and sodium iodide (1.3 mmol). The reactions were refluxed 14 hrs and after cooling filtered through a plug of celite. The crude materials were then concentrated down in vacuo to a form which was purified by flash chromatography (CH$_2$Cl$_2$/MeOH) and preparative chromatography.

EXAMPLE 49

General Procedure from Formula (XXXIV) Intermediate

A solution of the appropriate isocyanate derivative of Formula (XXXIV) (about 30 mmole) and aminoalkylpiperidine intermediate of Formula (XX) (about 40 mmole) in methylene chloride (500 mL) were stirred for several hrs. The reaction mixture was flash chromatographed in silica gel eluting with CH$_2$Cl$_2$–5 to 10% MeOH. Removal of solvent in vacuo affords the base of the Formula I compound which is then usually converted into salt form and purified.

EXAMPLE 50

1,4-Dihydro-[3-[[[[3-[4-(3-methoxyphenyl)-1-piperidinyl]propyl]amino]carbonyl]amino]phenyl]2,6-dimethyl-3,5-pyrinedicarboxylic acid dimethyl ester hydrochloride A solution of the (XXXIV) isocyanate intermediate (11.4 g, 33 mmol) and the (XX) propanamine intermediate (9.9 g, 40 mmol) in CH$_2$Cl$_2$ (500 mL) was stirred for 3 h. The reaction mixture was then directly chromatographed on silica gel by vacuum filtration. The desired product was eluted with CH$_2$Cl$_2$:MeOH 93:7 to 85:15. The solvent was removed in vacuo to afford a white foam (13.4 g, 69% yield). A portion of this material was taken up in EtOAc, and an equimolar quantity of 1N HCl in Et$_2$O was added in a dropwise fashion. Additional Et$_2$O was added, and the resulting precipitate was collected by filtration and dried overnight in an Abderhalden apparatus to furnish the salt as a white solid: mp 130°–135° C.; $^1$H NMR (DMSO-$d_6$) δ10.33 (br s, 1H), 8.95 (s, 1H), 8.74 (s, 1H), 7.24 (m, 2H), 7.10 (s, 1H), 7.02 (t, 1H, J=7.8 Hz), 6.78 (m, 3H), 6.65 (d, 1H, J=7.8 Hz), 6.49 (m, 1H), 4.84 (s, 1H), 3.73 (s, 3H), 3.54 (s, 6H), 3.48 (m, 2H), 3.35 (m, 1H), 3.15 (m, 2H), 3.03 (m, 3H), 2.76 (m, 1H), 2.25 (s, 6H), 1.97 (m, 6H); $^{13}$C NMR (DMSO-$d_6$): δ167.5, 159.4, 155.5, 148.1, 145.6, 140.3, 129.6, 128.2, 119.8, 118.7, 116.5, 115.5, 112.6, 111.7, 101.3, 55.0, 54.1, 52.0, 50.6, 37.9, 36.5, 30.0, 24.7, 18.2; Anal Calcd for $C_{33}H_{42}N_4O_6 \cdot HCl \cdot 0.5\ H_2O$: C, 62.30; H, 6.97; N, 8.81. Found: C, 62.46; H, 6.94; N, 8.71.

EXAMPLE 51

1,4Dihydro-2,6-dimethyl-4-[3-[[[[3-[4-[3-(2-propynyloxy)phenyl]-1-piperidinyl]-propyl]amino] carbonyl]amino]phenyl]-3,5-pyridinedicarboxylic acid dimethyl ester a) 4-[3-(2-Propynyloxy)phenyl]-1-piperidinepropanenitrile (XIX). A solution of 4-[3-(2-propynyloxy)phenyl]-1-piperidine (1.89 g, 8.79 mmol), acrylonitrile (0.51 g, 9.62 mmol) and MeCN (20 mL) was refluxed 1.5 h. After cooling to ambient temperature, the volatiles were removed in vacuo. The resulting amber oil was purified by flash chromatography ($SiO_2$: EtOAc/ hexane) to furnish 2.15 g (8.02 mmol, 91% yield) of (XIX) as a yellow oil: IR (film) 2248 and 2120 cm$^{-1}$; $^1$H NMR (DMSO-$d_6$) δ7.21 (m, 1H), 6.85 (m, 3H), 4.77 (d, 2H, J=2.4 Hz), 3.56 (t, 1H, J=2.4 Hz), 2.97 (m, 2H), 2.71 (m, 2H), 2.59 (m, 2H), 2.41 (m, 1H), 2.06 (m, 2H), and 1.61 (m, 4H); $^{13}$C NMR (DMSO-$d_6$) δ157.3, 147.8, 129.3, 120.1, 119.6, 117.5, 113.3, 112.3, 79.4, 78.1, 55.2, 53.1, 32.8, and 15.0. Anal. Calcd for $C_{17}H_{20}N_2O$: C, 76.09; H, 7.51; N, 10.44. Found: C, 75.83; H, 7.62; N, 10.36.

b) 1-(3-Aminopropyl)-4-[3-(2-propynyloxy)phenyl] piperidine (XX). To a solution of the nitrile (XIX) (2.00 g, 7.46 mmol) in THF (70 mL), was added $LiAlH_4$ (0.606 g, 15.9 mmol) in one portion and the resulting suspension was stirred under $N_2$ at room temperature for 1.5 h. The reaction was quenched by the successive addition of $H_2O$ (0.6 mL), 15% aq NaOH (0.6 mL) and $H_2O$ (2 mL). After filtration, the organic portion was washed with brine and dried over $K_2CO_3$. Filtration and concentration in vacuo afforded 1.5 g of the crude amine as a yellow oil. Purification by flash chromatography ($SiO_2$: ammoniated EtOAc/MeOH) furnished 0.462 g (1.70 mmol, 23% yield) of the diamine as a pale yellow oil: $^1$H NMR (CDCl$_3$) δ7.20 (m, 2H), 6.81 (m, 3H), 4.66 (m, 2H), 4.05 (br s, 2H), 3.13 (m, 2H), 3.02 (t, 2H, J=6.1 Hz), 2.49 (m, 4H), 2.20 (m, 2H), and 2.77 (m, 6H); $^{13}$C NMR (CDCl$_3$) δ157.6, 147.3, 129.3, 120.0, 113.6, 112.3, 78.6, 75.4, 57.8, 55.6, 54.1, 42.2, 41.3, 33.0, and 25.1. HRMS. Calcd for $C_{17}H_{25}N_2O$ (M+H): 273.1967. Found: 273.1970.

c) 1,4-Dihydro-2,6-dimethyl-4-[3-[[[[3-[4-[3-(2-propynyloxy)phenyl]-1-piperidinyl]propyl]amino]carbonyl] amino]phenyl]-3,5-pyridinedicarboxylic acid, dimethyl ester, hydrochloride salt, hemihydrate. To a solution of diamine intermediate (XX) (447 mg, 1.64 mmol) in $CH_2Cl_2$ (30 mL) was added isocyanate (XXXIV) (499 mg, 1.46 mmol) in one portion. After the solution was stirred for 2 h at room temperature, it was successively washed with $H_2O$, 1N HCl, $H_2O$, 1N NaOH, $H_2O$, and brine and then dried over $MgSO_4$. Filtration and concentration in vacuo gave 800 mg of crude product as a yellow oil. Purification of the oil by flash chromatography ($SiO_2$: ammoniated EtOAc/ MeOH) afforded 580 mg (0.945 mmol, 65% yield) of product as a colorless foam: mp indistinct; IR (KBr) 2121 cm$^{-1}$; $^1$H NMR (DMSO-$d_6$) δ8.88 (br s, 1H), 8.34 (br s, 1H), 7.24 (m, 2H), 7.10 (m, 1H), 7.03 (t, 1H, J=7.9 Hz), 6.81 (m, 2H), 6.66 (d, 1H, J=7.7 Hz), 6.04 (br t, 1H, J=5.6 Hz), 4.85 (s, 1H), 4.77 (d, 1H, J=5.2 Hz), 3.56 (s, 6H), 3.35 (m, 2H), 3.09 (m, 2H), 2.97 (d, 2H, J=10.8 Hz), 2.45 (m, 1H), 2.32 (m, 2H), 2.26 (s, 6H), 1.96 (m, 2H), and 1.65 (m, 6H); $^{13}$C NMR (DMSO-$d_6$) δ167.5, 157.3, 155.3, 148.2, 145.7, 140.4, 129.4, 128.3, 119.7, 116.4, 115.5, 113.4, 112.3, 101.4, 79.5, 78.2, 55.8, 55.3, 53.9, 50.7, 42.1, 39.8, 38.5, 37.6, 33.0, 27.3, and 18.3. Anal. Calcd for $C_{35}H_{42}N_4O_6 \cdot 0.5\ H_2O$: C, 67.35; H, 6.95; N, 8.98. Found: C, 67.26; H, 6.71; N, 8.94.

EXAMPLE 52

1,4-Dihydro-2,6-dimethyl-4-[3-[[[[3-[4-[3-(2-propoxy)phenyl]-1-piperidinyl]-propyl]amino] carbonyl]amino]phenyl]-3,5-pyridinedicarboxylic acid, dimethyl ester A suspension of the product of Example 51 (316 mg, 0.519 mmol) and 81 mg of 10% Pd/C in EtOAc (65 mL) was shaken under 50 psi of $H_2$ on a Parr Hydrogenator for 3 h. The suspension was then filtered through Celite and the filtrate concentrated in vacuo to give 325 mg of the product as a clear oil. This residue was purified by preparative HPLC (Zorbax-RX-C8 column; 45% MeCN/55% 0.1% TFA $H_2O$; 4.2 mL/min) and the free base subsequently converted to the HCl salt to furnish the product as a colorless foam: mp 110°–130° C. (sintered); $^1$H NMR (CDCl$_3$) δ10.62 (br s, 1H). 8.53 (br s, 1H), 7.34 (d, 1H, J=7.6 Hz), 7.12 (m, 3H), 7.00 (t, 1H, J=7.6 Hz), 6.86 (d, 1H, J=7.5 Hz), 6.68 (m, 4H), 4.90 (s, 1H), 3.82 (t, 2H, J=6.5 Hz), 3.54 (s, 6H), 3.45 (m, 2H), 3.20 (m, 2H), 2.75 (m, 4H), 2.62 (m, 3H), 2.25 (s, 6H), 1.92 (m, 4H), 1.72 (h, 2H, J=6.8 Hz), and 0.95 (t, 3H, J=7.3 Hz); $^{13}$C NMR (CDCl$_3$) δ168.4, 159.4, 157.1, 148.8, 145.5, 144.4, 139.6, 129.8, 128.5, 122.0, 118.7, 118.1, 117.2, 113.6, 112.5, 102.9, 69.5, 55.2, 53.3, 51.0, 40.2, 39.1, 36.7, 30.2, 25.1, 22.6, 19.2, and 10.5. Anal. Calcd for $C_{35}H_{46}N_4O_6 \cdot HCl \cdot 0.45 H_2O$: C, 63.37; H, 7.28; N, 8.45. Found: C, 63.37; H, 7.40; N, 8.28.

The following examples of Formula I compounds were prepared using the processes of Example 48.

EXAMPLE 53

1,4-Dihydro-4-[3-[[[[3-[4-(3-methoxyphenyl) piperidin-1-yl]amino]carbonyl]amino]phenyl]-2,6-dimethyl-3,5-pyridine dicarboxylic acid dimethyl ester This compound was isolated as an orange-yellow solid in 51% yield (method B) mp 240° C.; $^1$H NMR (DMSO-$d_6$) δ8.85 (s, 1H), 8.48 (s, 1H), 7.31–7.26 (m, 2H), 7.08–6.97 (m, 4H), 6.85–6.82 (m, 1H), 6.68–6.62 (m, 1H), 6.22 (t, 1H, J=6 Hz), 5.48 (s,1H), 4.84 (s, 1H), 3.75 (s, 3H), 3.54 (s, 6H), 3.50–3.45 (m, 2H), 3.30–3.18 (m, 6H), 2.27 (s, 6H), 2.24–2.17 (m, 2H), 1.85–1.80 (m, 4H); $^{13}$C NMR (DMSO-$d_6$) δ167.5, 166.0, 159.2, 155.5, 149.4, 148.2, 145.6, 140.1, 129.4, 128.3, 120.0, 116.7, 115.6, 112.1, 110.7, 101.4, 67.9, 55.1, 53.9, 50.7, 48.6, 36.5, 35.2, 34.4, 24.9, 18.2; HRMS Calcd. for $C_{33}H_{43}N_4O_7$ (M+H): 607.3132. Found: 607.3125.

EXAMPLE 54

1,4-Dihydro-4-[3-[[[[3-[4-(2-methoxyphenyl) piperidin-1-yl]propyl]amino]carbonyl]amino] phenyl]-2,6-dimethyl-3,5-pyridine dicarboxylic acid dimethyl ester This compound was isolated as a light brown solid in 7% yield (method B): mp 128°–132° C. $^1$H NMR (DMSO-$d_6$)

δ 8.86 (s, 1H), 8.36 (s, 1H), 7.05 (m, 7H), 6.65 (d, 1H, J=8 Hz), 6.08 (br.s., 1H), 4.84 (s, 1H), 3.75 (s, 3H), 3.54 (s, 6H), 3.07 (m, 4H), 2.86 (m, 1H), 2.40 (m, 2H), 2.24 (s, 6H), 2.04 (br.s., 2H), 1.61 (m, 6H); $^{13}$C NMR (DMSO-d$_6$) δ167.5, 156.5, 155.2, 148.1, 145.6, 140.4, 133.6, 128.2, 126.9, 126.2, 120.5, 119.7, 116.4, 115.5, 110.7, 101.4, 55.6, 55.3, 53.9, 50.7, 37.4, 34.6, 31.5, 27.0, 18.2; HRMS Calcd. for C$_{33}$H$_{43}$N$_4$O$_6$ (M+H): 591.3183. Found: 591.3161.

EXAMPLE 55

1,4-Dihydro-4-[3-[[[[3-[4-phenylpiperidin-1-yl)propyl]amino]carbonyl]amino]phenyl]-2,6-dimethyl-3,5-pyridinedicarboxylic acid, dimethyl ester, fumarate salt This compound was isolated as a light yellow solid in 18% yield (method A): mp 210° C.; $^1$H NMR (DMSO-d$_6$) δ8.92 (s, 1H), 8.80 (s, 1H), 7.35–6.97 (m, 9H), 6.68–6.66 (m, 1H), 6.98 (s, 2H), 4.87 (s, 1H), 3.57 (s, 6H), 3.33–3.29 (m, 2H), 3.15–3.14 (m, 2H), 2.81–2.47 (m, 5H), 2.27 (s, 6H), 1.88–1.74 (m, 6H); $^{13}$C NMR (DMSO-d$_6$) δ167.5, 167.4, 155.5, 148.1, 145.6, 145.2, 140.5, 134.8, 128.5, 128.2, 126.6, 126.3, 119.7, 116.5, 115.5, 101.4, 54.5, 52.6, 50.6, 36.9, 31.2, 25.8, 18.2; Anal. Calcd. for C$_{32}$H$_{40}$N$_4$O$_5$·1.0 C$_4$H$_4$O$_4$·1.6 H$_2$O: C, 61.28; H, 6.74; N, 7.94 Found: C, 61.68; H, 6.57; N, 7.54.

EXAMPLE 56

1,4-Dihydro-4-[3-[[[[3-(4-hydroxy-4-phenylpiperidin-1-yl)propyl]amino]carbonyl]amino]phenyl-2,6-dimethyl-3,5-pyridine dicarboxylic acid, dimethyl ester, fumarate salt This compound was isolated as a light yellow solid in 53% yield (method B): mp 238°–242° C.; $^1$H NMR (DMSO-d$_6$) δ8.85 (s, 1H), 8.50 (s, 1H), 7.34 (m, 6H), 7.04 (m, 2H), 6.66 (d, 1H, J=7.6 Hz), 6.61 (s, 2H), 6.23 (t, 1H, J=5.6 Hz), 4.83 (s, 1H), 3.34 (m, 10H), 2.49 (s, 1H), 2.20 (m, 7H), 1.79 (m, 4H); $^{13}$C NMR (DMSO-d$_6$) δ167.5, 166.0, 155.5, 148.2, 145.6, 140.1, 134.0, 128.2, 126.9, 124.5, 120.0, 116.6, 115.6, 101.4, 67.8, 56.0, 53.9, 50.7, 48.5, 36.4, 35.2, 24.9, 18.6, 18.2; HRMS Calcd. for C$_{32}$H$_{41}$N$_4$O$_6$ (M+H): 577.3026. Found: 577.3019.

EXAMPLE 57

1,4-Dihydro-4-[3-[[[[3-[4-cyano-4-phenylpiperidin-1-yl]propyl]amino]carbonyl]amino]phenyl]-2,6-dimethyl-3,5-pyridine dicarboxylic acid, dimethyl ester, fumarate salt This compound was obtained as a white solid in 53% yield (method B): mp 205°–210° C.; $^1$H NMR (DMSO-d$_6$) δ8.86 (s, 1H), 8.40 (s, 1H), 7.53–7.33 (m, 5H), 7.24–7.22 (m, 1H), 7.09 (s, 1H), 7.01 (t, 1H, J=8 Hz), 6.66–6.63 (m, 1H), 6.60 (s, 2H), 6.12 (br s, 1H), 4.84 (s, 1H), 3.53 (s, 6H), 3.11–3.07 (m, 4H), 2.52–2.48 (m, 3H), 2.37 (t, 2H, J=11 Hz), 2.24 (s, 6H), 2.16–2.01 (m, 3H), 1.66–1.61 (m, 2H); $^{13}$C NMR (DMSO-d$_6$) δ167.5, 166.3, 155.3, 148.1, 145.6, 140.4, 140.1, 134.2, 129.1, 128.2, 128.1, 125.6, 122.1, 119.8, 116.4, 115.5, 101.4, 55.1, 50.7, 50.3, 41.7, 37.4, 35.1, 26.7, 18.2; Anal. Calcd. for C$_{33}$H$_{39}$N$_5$O$_5$·1.0 C$_4$H$_4$O$_4$·0.4 H$_2$O: C, 62.68; H, 6.23; N, 9.88. Found: C, 62.29; H, 6.16; N, 9.63.

EXAMPLE 58

1,4-Dihydro-4-[3-[[[[3-[4-(3-hydroxyphenyl)piperidin-1-yl]propyl]amino]carbonyl]amino]phenyl]-2,6-dimethyl-3,5-pyridine dicarboxylic acid, dimethyl ester, fumarate salt This compound was isolated as an off-white solid in 16% yield (method B): mp 142°–148° C.; $^1$H NMR (DMSO-d$_6$) δ8.88 (s, 1H), 8.71 (s, 1H), 7.29 (m, 1H), 7.05 (m, 3H), 6.60 (m, 8H), 4.83 (s, 1H), 3.54 (s, 6H), 3.26 (m, 2H), 3.11 (m, 2H), 2.71 (m, 2H), 2.50 (m, 3H), 2.24 (s, 6H), 1.76 (m, 6H); $^{13}$C NMR (DMSO-d$_6$) δ167.5, 157.5, 155.5, 148.1, 146.7, 145.6, 140.4, 134.8, 129.4, 128.2, 119.7, 117.2, 116.5, 115.5, 113.5, 113.2, 101.4, 54.6, 52.7, 50.7, 31.3, 25.8, 18.2; Anal Calcd. for C$_{32}$H$_{40}$N$_4$O$_6$·1.0 C$_4$H$_4$O$_4$·1.4 H$_2$O: C, 60.22; H, 6.57; N, 7.80. Found: C, 59.84; H, 6.43; N, 7.57. HRMS Calcd. for C$_{32}$H$_{41}$N$_4$O$_6$ (M+H): 577.3026. Found: 577.3013.

EXAMPLE 59

1,4-Dihydro-4-[3-[[[[3-[4-naphthalen-1-ylpiperidin-1-yl)propyl]amino]carbonyl]amino]phenyl]-2,6-dimethyl-3,5-pyridine dicarboxylic acid, dimethyl ester, fumarate salt This compound was isolated as a white solid in 25% yield Method B): mp 214°–218° C.; $^1$H NMR (DMSO-d$_6$) δ8.88 (s, 1H), 8.79 (s, 1H), 8.17 (d, 1H, J=8 Hz),7.93–7.91 (m, 1H), 7.79–7.77 (m, 1H), 7.58–7.27 (m, 4H), 7.12–6.99 (m, 2H), 6.67–6.64 (m, 2H), 6.56 (s, 2H), 4.85 (s, 1H), 3.54 (s, 6H), 3.47–3.30 (m, 2H), 3.15 (br s, 2H), 2.83–2.81 (m, 4H), 2.67 (m, 1H), 2.25 (s, 6H), 2.03–1.97 (m, 3H), 1.78–1.76 (m, 3H); $^{13}$C NMR (DMSO-d$_6$) δ167.5, 155.5, 148.1, 145.6, 140.9, 140.5, 134.8, 133.5, 130.8, 128.8, 128.2, 126.7, 126.1, 125.7, 125.6, 122.9, 122.4, 119.7, 116.5, 115.5, 101.4, 54.5, 52.7, 50.6, 36.9, 35.2, 30.9, 25.7, 18.2; Anal. Calcd. for C$_{36}$H$_{42}$N$_4$O$_5$·1.0 C$_4$H$_4$O$_4$·1.0 H$_2$O: C, 64.50; H, 6.50; N, 7.52. Found: C, 64.24; H, 6.33; N, 7.31.

EXAMPLE 60

4-[3-[[[[3-[4-(1,1-Biphenyl-3-yl)piperidin-1-yl]propyl]amino]carbonyl]amino]phenyl]-1,4-dihydro-2,6-dimethyl-3,5-pyridine dicarboxylic acid, dimethyl ester This compound was isolated as an off-white solid in 6% yield (method B): mp 108°–112° C.; $^1$H NMR (DMSO-d$_6$) δ8.85 (s, 1H), 8.33 (s, 1H), 7.65 (m, 2H), 7.40 (m, 6H), 7.23 (d, 2H, J=8 Hz), 7.10 (s, 1H), 7.01 (t, 1H, J=8 Hz), 6.65 (d, 1H, J=6 Hz), 6.05 (m, 1H), 4.84 (s, 1H), 3.54 (s, 6H), 3.10 (m, 2H), 2.98 (m, 2H), 2.55 (m, 1H), 2.33 (t, 2H, J=7 Hz), 2.24 (s, 6H), 1.98 (m, 2H), 1.67 (m, 6H); $^{13}$C NMR (DMSO-d$_6$) δ167.5, 155.2, 148.1, 147.1, 145.6, 140.3, 128.9, 128.9, 128.2, 127.3, 126.8, 125.8, 125.3, 124.5, 119.7, 116.4, 115.4, 101.4, 55.8, 53.9, 50.7, 42.1, 33.1, 27.2, 18.2; Anal. Calcd. for C$_{38}$H$_{44}$N$_4$O$_5$·0.8 H$_2$O: C, 70.09; H, 7.06; N, 8.60. Found: C, 69.76; H, 7.11; N, 8.62.

EXAMPLE 61

1,4-Dihydro-4-[3-[[[[3-[4-(phenylmethyl)-piperidin-1-yl]propyl]amino]carbonyl]amino]phenyl-2,6-dimethyl-3,5-pyridinedicarboxylic acid, dimethyl ester, fumarate salt This compound was isolated as a tan solid in 58% yield (method B): mp 223°–227° C.; $^1$H NMR (DMSO-d$_6$) δ8.89 (s, 1H), 8.84 (s, 1H), 7.29–6.98 (m, 8H), 6.68–6.62 (m, 2H), 6.54 (s, 2H), 4.83 (s, 1H), 3.54 (s, 6H), 3.22–3.19 (m, 2H), 3.09–3.08 (m, 2H), 2.76 (t, 2H, J=7 Hz), 2.51–2.47 (m, 4H), 2.24 (s, 6H), 1.70–1.62 (m, 4H), 1.41–1.13 (m, 2H); $^{13}$C NMR (DMSO-d$_6$) δ167.5, 167.5, 155.6, 148.1, 145.7, 140.5, 139.9, 134.9, 129.1, 128.3, 128.2, 125.9, 119.7, 116.5, 115.5, 101.4, 54.2, 51.9, 50.7, 41.6, 36.8, 35.7, 29.7, 29.4, 25.3, 18.4; Anal Calcd. for C$_{33}$H$_{42}$N$_4$O$_5$·1.0 C$_4$H$_4$O$_4$·0.5 H$_2$O: C, 63.50; H, 6.77; N, 8.01. Found: C, 63.14; H, 6.74; N, 7.76.

EXAMPLE 62

4-[3-[[[[3-(4-cyclohexyl-1-piperidinyl)propyl]amino]carbonyl]amino]phenyl]-1,4-dihydro-2,6-dimethyl-3,5-pyridinedicarboxylic acid, dimethyl ester, hydrochloride salt This compound was isolated as a white solid in 6% yield (method B): mp 198°–200° C. (dec.); $^1$H NMR (DMSO-$d_6$): δ10.05 (br s, 1H), 8.98 (s, 1H), 8.79 (s, 1H), 7.26 (d, 1H, J=8.1 Hz), 7.09 (s, 1H), 7.01 (t, 1H, J=8.1 Hz), 6.65 (d, 1H, J=7.8 Hz), 6.54 (t, 1H, J=5.7 Hz), 4.83 (s, 1 H), 3.54 (s, 6H), 3.43 (d, 2H, J=12.0 Hz), 3.13 (m, 2H), 2 99 (m, 2H), 2.79 (m, 2H), 2.25 (s, 6H), 1.80 (m, 4H), 1.62 (m, 8H), 1.25 (m, 2H), 1.14 (m, 2H), 0.90 (m, 2H); $^{13}$C NMR (DMSO-$d_6$) δ167.5, 155.5, 148.1, 145.7, 140.3, 128.2, 119.8, 116.5, 115.4, 101.3, 54.0, 52.1, 50.6, 41.4, 38.4, 36.4, 29.4, 26.1, 26.0, 24.6, 18.2. Anal Calcd. for $C_{32}H_{46}N_4O_5$. 1.0 HCl.1.5 $H_2O$: C, 60.99; H, 8.00; N, 8.89. Found: C, 60.71; H, 7.74; N, 8.79.

EXAMPLE 63

1,4-dihydro-4-[3-[[[[3-[4-hydroxy-4-(2-phenoxyphenyl)-1-piperidinyl]propyl]amino]carbonyl]amino]phenyl]-2,6-dimethyl-3,5-pyridinedicarboxylic acid, dimethyl ester, hydrochloride salt This compound was isolated as a white solid in 23% yield (method B): mp 145°–155° C.; $^1$H NMR (DMSO-$d_6$) δ9.69 (br s, 1H), 8.95 (s, 1H), 8.77 (s, 1H), 7.71 (d, 1H, J=6.9 Hz), 7.39 (t, 2H, J=7.8 Hz), 7.11 (m, 8H), 6.64 (t, 2H, J=11.4 Hz), 6.55 (br s, 1H), 5.63 (s, 1H), 4.82 (s, 1H), 3.53 (s, 6H), 3.28 (m, 4H), 3.09 (m, 4H), 2.71 (t, 2H, J=12.6 Hz), 2.23 (s, 6H), 1.80 (m, 4H); $^{13}$C NMR (DMSO-$d_6$) δ167.4, 156.6, 155.5, 154.2, 148.1, 145.7, 140.2, 130.0, 128.8, 128.2, 127.5, 123.6, 123.0, 119.7, 118.6, 116.4, 115.4, 101.3, 68.0, 50.6, 48.1, 38.4, 36.4, 32.7, 24.6, 18.2. Anal Calcd. for $C_{38}H_{44}N_4O_7$.HCl.2 $H_2O$: C, 61.57; H, 6.66; N, 7.56. Found: C, 61.51; H, 6.57; N, 7.32.

EXAMPLE 64

1,4-Dihydro-4-[3-[[[[3-[1,2,3,6-tetrahydro-4-(3-methoxyphenyl)pyridin-1-yl]propyl]amino]carbonyl]amino]phenyl]-2,6-dimethyl-3,5-pyridine dicarboxylic acid, dimethyl ester This compound was isolated as an orange solid in 16% yield (method B): mp 95°–100° C.; $^1$H NMR (DMSO-$d_6$) δ8.86 (s, 1H), 8.36 (s, 1H), 7.11 (m, 6H), 6.8 (d, 1H, J=8 Hz), 6.64 (d, 1H, J=8 Hz), 6.00 (m, 2H), 4.83 (s, 1H), 3.74 (s, 1H), 3.54 (s, 3H), 3.33 (s, 6H), 3.10 (m, 2H), 2.48 (m, 11H), 2.24 (s, 3H), 1.61 (m, 1H); HRMS Calcd. for $C_{33}H_{41}N_4O_6$ (M+H): 589.3026. Found: 589.3033.

EXAMPLE 65

1,4-Dihydro-4-[3-[[[[3-(1,2,3,6-tetrahydro-4-phenylpyridin-1-yl)propyl]amino]carbonyl]amino]phenyl]-2,6-dimethyl-3,5-pyridine dicarboxylic acid, dimethyl ester, fumaric salt This compound was isolated as a yellow solid in 42% yield (method B): mp 130° C.; $^1$H NMR (CDCl$_3$) δ7.36–7.20 (m, 6H), 7.06–6.91 (m, 5H), 6.30 (s, 1H), 6.01 (s, 1H), 5.62 (s, 1H), 4.94 (s, 1H), 3.59 (s, 6H), 3.26–3.25 (m, 2H), 3.09–3.08 (m, 2H), 2.67–2.63 (m, 2H), 2.52–2.47 (m, 4H), 2.23 (s, 6H), 1.74–1.68 (m, 2H); $^{13}$C NMR (DMSO-$d_6$) δ168.1, 156.5, 148.6, 144.8, 140.5, 138.9, 134.9, 128.7, 128.3, 127.1, 124.8, 122.8, 121.4, 119.9, 118.7, 103.3, 53.1, 50.9, 50.1, 39.2, 27.7, 26.9, 19.3; Anal. Calcd. for $C_{32}H_{38}N_4O_5$.0.4 $C_4H_4O_4$: C, 66.69; H, 6.60; N, 9.26. Found: C, 66.29; H, 6.36; N, 9.70; HRMS Calcd. for $C_{32}H_{39}N_4O_5$ (M+H): 559.2921. Found: 559.2908.

EXAMPLE 66

1,4-Dihydro-4-[3-[[[[3-[1,2,3,6-tetrahydro-4-(3-hydroxyphenyl)pyridine]propyl]amino]carbonyl]amino]phenyl]-2,6-dimethyl-3,5-pyridine dicarboxylic acid, dimethyl ester This compound was isolated as an orange solid in 39% yield (method B): mp 232° C.

EXAMPLE 67

1,4-Dihydro-4-[3-[[[[3-[1,2,3,6-tetrahydro-4-(1-naphthalenyl)-1-pyridinyl]propyl]amino]carbonyl]amino]phenyl-2,6-dimethyl-3,5-pyridinedicarboxylic acid, dimethyl ester, fumaric salt This compound was isolated as a tan solid in 24% yield (method B): mp 225° C.; $^1$H NMR (DMSO-$d_6$) δ8.91 (s, 1H), 8.68 (s, 1H), 8.04–8.01 (m, 1H), 7.96–7.93 (m, 1H), 7.88–7.85 (m, 1H), 7.54–7.47 (m, 3H), 7.34–7.30 (m, 2H), 7.15 (s, 1H), 7.05 (t, 1H, J=8 Hz), 6.70–6.67 (m, 1H), 6.61 (s, 2H), 6.47 (brs, 1H), 5.74 (s, 1H), 4.84 (s, 1H), 3.57–3.53 (m, 8H), 3.20 (s, 2H), 3.11 (s, 2H), 2.86 (m, 2H), 2.61 (br s, 2H), 2.28 (s, 6H), 2.06–1.83 (m, 2H); Anal. Calcd. for $C_{36}H_{40}N_4O_5$.1.0 $C_4H_4O_4$ 1.3 $H_2O$.0.1 $C_2H_5OH$: C, 64.79; H, 5.96; N, 7.26. Found: C, 64.53; H, 6.26; N, 7.06; HRMS Calcd. for $C_{36}H_{41}N_4O_5$ (M+H): 609.3077. Found: 609.3067.

EXAMPLE 68

1,4-Dihydro-4-[3-[[[[3-(4-phenyl-1-piperidinyl)propyl]amino]carbonyl]amino]phenyl]-2,6-dimethyl-3,5-pyridinedicarboxylic acid, ethyl methyl ester, hydrochloride salt This compound was isolated as a tan solid in 48% yield (method A): mp 88°–92° C.; $^1$H NMR (DMSO-$d_6$) δ8.94 (s, 1H), 8.80 (s, 1H), 7.25 (m, 6H), 7.10 (s, 1H), 7.03 (t, 1H, J=7.6 Hz), 6.65 (d, 1H, J=7.1 Hz), 6.30 (br s, 1H), 4.81 (s, 1H), 3.98 (m, 2H), 3.52 (s, 3H), 3.21 (m, 2H), 3.06 (m, 6H), 2.75 (m, 2H), 2.24 (s, 3H), 2.23 (s, 3H), 2.10 (m, 2H), 1.88 (m, 3H), 1.29 (t, 3H, J=6.7 Hz).

EXAMPLE 69

1,4-Dihydro-4-[3-[[[[3-[(4-phenylmethyl-1-piperidinyl]propyl]amino]carbonyl]amino]phenyl]-2,6-dimethyl-3,5-pyridinedicarboxylic acid, ethyl methyl ester, fumarate salt This compound was isolated as a white solid in 57% yield (method A): mp 228°–230° C.; $^1$H NMR (DMSO-$d_6$) δ8.89 (s, 1H), 8.82 (s, 1H), 7.30–7.14 (m, 6H), 7.09 (s, 1H), 6.99 (t, 1H, J=7.8 Hz), 6.65 (m, 2H), 6.57 (s, 2H), 4.81 (s, 1H), 4.04–3.93 (m, 2H), 3.52 (s, 3H), 3.40–3.33 (m, 2H), 3.31–3.09 (m, 2H), 2.92–2.87 (m, 2H), 2.69 (t, 2H, J=11 Hz), 2.52–2.47 (m, 2H), 2.24 (d, 6H, J=3 Hz), 1.80–1.65 (m, 5H), 1.51–1.39 (m, 2H), 1.13 (t, 3H, J=7 Hz); $^{13}$C NMR (DMSO-$d_6$) δ167.5, 167.0, 166.9, 155.6, 148.3, 145.6, 145.2, 140.3, 139.6, 134.5, 128.9, 128.3, 128.0, 125.9, 119.9, 116.6, 115.4, 101.7, 101.3, 58.9, 53.8, 51.4, 50.6, 41.3, 36.5, 35.1, 28.7, 24.9, 18.2, 14.3; HRMS Calcd. for $C_{34}H_{45}N_4O_5$ (M+H): 589.3390. Found: 589.3378.

EXAMPLE 70

1,4-Dihydro-4-[3-[[[[3-[4-hydroxy-4-(2-methoxyphenyl)-piperidin-1-yl]propyl]amino]carbonyl]amino]phenyl]-2,6-dimethyl-3,5-pyridinedicarboxylic acid, ethyl methyl ester, hydrochloride This compound was isolated as a light yellow solid in 53% yield (method B): mp 210°–215° C.; $^1$H NMR (CDCl$_3$) δ9.98 (brs, 1H), 8.34 (s, 1H), 7.39–7.12 (m, 4H), 7.07–6.85 (m, 4H), 6.63 (s, 2H), 4.90 (s, 1H), 4.06–3.99 (m, 2H), 3.88 (s, 3H), 3.57 (s, 3H), 3.28–3.20 (m, 6H, 2.98 (brs, 2H), 2.52–2.50 (m, 2H), 2.31–2.26 (m, 6H), 2.15–2.11 (m, 2H), 1.96 (m, 2H), 1.18 (t, 3H, J=7 Hz); $^{13}$C NMR (CDCl$_3$) δ168.3, 167.9, 157.7, 156.7, 148.8, 154.2, 144.9, 139.0, 131.8, 129.3, 128.2, 125.5, 122.5, 121.4, 118.5, 117.1, 111.4, 103.4, 103.0, 68.9, 59.8, 55.5, 54.5, 50.9, 48.9, 39.2, 36.2, 33.3, 19.4, 14.3; Anal. Calcd. for $C_{34}H_{44}N_4O_7 \cdot 1.0$ HCl.1.0 H$_2$O: C, 60.48; H, 7.02; N, 8.30. Found: C, 60.87; H, 7.23; N, 8.05.

EXAMPLE 71

1,4-Dihydro-4-[8-[[[[3-[4-hydroxy-4-(3-methoxyphenyl)-piperidin-1-yl]propyl]amino]carbonyl]amino]phenyl]-2,6-dimethyl-3,5-pyridinedicarboxylic acid, ethyl methyl ester, fumarate salt This compound was partially purified in 5% yield (method B): mp 210°–214° C.; $^1$H NMR (DMSO-d$_6$) δ8.85 (s, 1H), 8.80 (s, 1H), 7.39–7.20 (m, 2H), 7.11 (s, 1H), 7.03–6.98 (m, 3H), 6.81–6.78 (m, 1H), 6.67–6.65 (m, 2H), 6.55 (s, 4H), 4.80 (s, 1H), 4.04–3.91 (m, 2H), 3.73 (s, 3H), 3.53 (s, 3H), 3.26–2.97 (m, 8H), 2.24–2.19 (m, 8H), 1.81–1.69 (m, 4H); $^{13}$C NMR (DMSO-d$_6$) δ167.5, 167.3, 167.0, 159.1, 155.5, 150.1, 148.3, 145.6, 145.2, 140.4, 134.8, 129.1, 128.1, 119.9, 116.8, 116.7, 115.5, 111.9, 110.7, 101.8, 101.3, 68.4, 59.0, 54.9, 50.6, 48.2, 35.4, 25.1, 18.3, 14.3; HRMS Calcd. for $C_{34}H_{45}N_4O_7$ (M+H): 621.3288. Found: 621.3304.

EXAMPLE 72

1,4-Dihydro-4-[3-[[[[2-[4-(3-methoxyphenyl)-1-piperidinyl]ethyl]amino]carbonyl]amino]phenyl]-2,6-dimethyl-3,5-pyridinedicarboxylic acid, dimethyl ester hydrochloride This material was obtained as a cream solid in 77% yield: mp 115°–120° C.; $^1$H NMR (DMSO-d$_6$) δ10.14 (br s, 1H), 8.96 (s, 1H), 8.69 (s, 1H), 7.27 (m, 2H), 7.15 (s, 1H), 7.05 (t, 1H, J=7.8 Hz), 6.82 (m, 3H), 6.68 (d, 1H, J=7.8 Hz), 6.62 (m, 1H), 4.86 (s, 1H), 3.75 (s, 3H), 3.63 (m, 2H), 3.56 (s, 6H), 3.51 (m, 2H), 3.17 (m, 2H), 3.07 (m, 2H), 2.79 (m, 1H), 2.26 (s, 6H), 1.98 (m, 4H); $^{13}$C NMR (DMSO-d$_6$) δ167.4, 159.4, 155.5, 148.1, 145.8, 145.6, 140.0, 129.6, 128.2, 120.0, 118.6, 116.7, 115.6, 112.6, 111.7, 101.3, 56.3, 54.9, 52.4, 50.6, 38.4, 34.2, 29.8, 18.2. Anal. Calcd for $C_{32}H_{40}N_4O_6 \cdot$HCl.0.6 H$_2$O.0.25 CH$_2$Cl$_2$: C, 60.04; H, 6.67; N, 8.68. Found: C, 59.87; H, 6.27; N, 8.40.

EXAMPLE 73

1,4-Dihydro-4-[3-[[[[4-[4-(3-methoxyphenyl)-1-piperidinyl]butyl]amino]carbonyl]amino]phenyl]-2,6-dimethyl-3,5-pyridinedicarboxylic acid, dimethyl ester hydrochloride This compound was obtained as a white solid in 53% yield: mp 125°–130° C.; $^1$H NMR (DMSO-d$_6$) δ10.29 (br s, 1H), 9.01 (s, 1H), 8.96 (s, 1H), 7.26 (m, 2H), 7.11 (s, 1H), 7.03 (t, 1H, J=7.8 Hz), 6.82 (m, 3H), 6.65 (d, 1H, J=7.8 Hz), 6.42 (t, 1H, J=5.7 Hz), 4.85 (s, 1H), 3.74 (s, 3H), 3.56 (s, 6H), 3.53 (m, 2H), 3.10 (m, 4H), 3.01 (m, 2H), 2.79 (m, 1H), 2.26 (s, 6H), 2.03 (m, 4H), 1.75 (m, 2H), 1.47 (m, 2H); $^{13}$C NMR (DMSO-d$_6$) δ167.4, 159.4, 155.4, 148.1, 145.9, 145.6, 140.4, 129.6, 128.2, 119.6, 118.6, 116.3, 115.3, 112.6, 111.7, 55.6, 54.9, 51.9, 50.6, 38.7, 38.3, 29.7, 27.1, 20.7, 19.1, 18.2. Anal. Calcd for $C_{34}H_{44}N_4O_6 \cdot$HCl.0.75 H$_2$O: C, 62.38; H, 7.16; N, 8.56. Found: C, 62.51; H, 6.82; N, 8.20.

EXAMPLE 74

Quaternary Salt Formation

1-[3-[[[[1,4-Dihydro-3,5-bis(methoxycarbonyl)-2,6-dimethyl-4-pyridinyl]phenyl]amino]carbonyl]amino]propyl]-4-(3-methoxyphenyl)-1-methylpiperidinium iodide. A solution of the Formula I base of Example 50 (743 mg, 1.26 mmol), excess methyl iodide (5.79 g, 40.8 mmol), and 25 mL of THF was stirred at room temperature for 3 days. After the addition of Et$_2$O (50 mL), the solid was collected by filtration and then recrystallized from aq i-PrOH to furnish 545 mg (0.745 mmol, 59% yield) of quaternary product as a yellow solid: mp 222°–224° C. (with gas evolution); $^1$H NMR (DMSOd$_6$) δ8.84 (s, 1H), 8.45 (s, 1H), 7.27 (m, 1H), 7.23 (t, 1H, J=8.2 Hz), 7.07 (m, 1H), 7.03 (t, 1H, J=7.9 Hz), 6.90 (m, 2H), 6.79 (m, 1H), 6.66 (d, 1H, J=7.7 Hz), 6.17 (br t, 1H, J=5.8 Hz), 4.84 (s, 1H), 3.74 (s, 3H), 3.54 (s, 6H), 3.52 (m, 2H), (m, 4H), 3.15 (m, 2H), 3.10 (s, 3H), 2.80 (m, 1H), 2.23 (s, 6H), 2.06 (m, 2H), and 1.91 (m, 4H); $^{13}$C NMR DMSOd$_6$) δ167.5, 159.5, 155.3, 148.1, 145.5, 145.4, 140.1, 129.5, 129.2, 120.0, 119.2, 116.6, 115.6, 112.8, 111.9, 101.4, 65.6, 60.1, 55.1, 50.7, 43.7, 38.9, 38.5, 36.5, 26.7, 22.8, and 18.2. Anal. Calcd for $C_{34}H_{44}N_4O_6 \cdot$I: C, 55.82; H, 6.06; N, 7.66. Found: C, 55.49; H, 6.35; N, 7.47.

3. B is NR$^1$

EXAMPLE 75

1,4-Dihydro-4-[3-[[[[3-[4-(3-methoxyphenyl)-1-piperidinyl]propyl]methylamino]carbonyl]amino]phenyl]-2,6-dimethyl-3,5-pyridinedicarboxylic acid, dimethyl ester hydrochloride

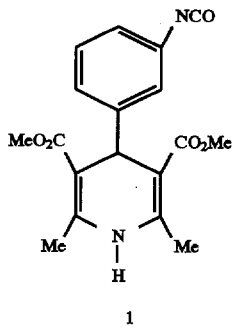

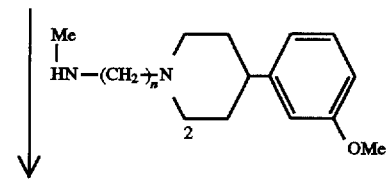

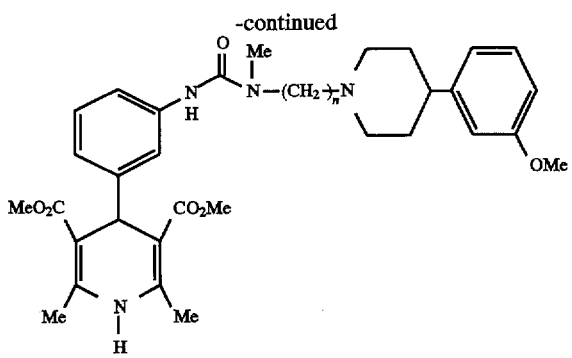

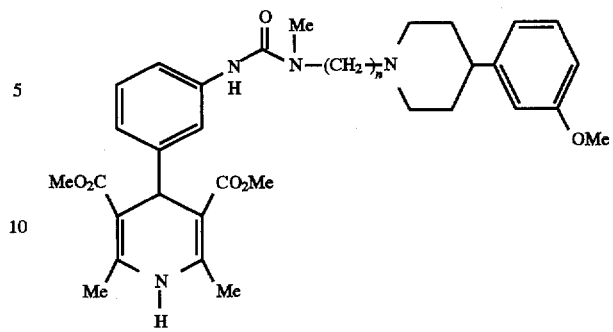

General Coupling Procedure

A solution of the isocyanate 1 (10 mmol) and the appropriate amine 2 (12 mmol) in CH$_2$Cl$_2$ (500 mL) was stirred for 3 h at room temperature. After concentration in vacuo, the residue was purified by chromatography (SiO$_2$: MeOH:CH$_2$Cl$_2$). This material was taken up in EtOAc and an equimolar quantity of 1N HCl in Et$_2$O was added in a dropwise fashion to form the salt. Additional Et$_2$O was subsequently added and the resulting precipitate collected by filtration and dried overnight to furnish the hydrochlorides salts. In this manner the following compound was obtained as a white solid in 43% yield: mp >130° C. (dec); $^1$H NMR (DMSO-d$_6$) δ10.58 (br s, 1H), 8.96 (s, 1H), 8.25 (s, 1H), 7.23 (m, 3H), 7.03 (t, 1H, J=7.8 Hz), 6.79 (m, 3H), 6.70 (d, 1H, J=7.5 Hz), 4.85 (s, 1H), 3.72 (s, 3H), 3.53 (m, 8H), 3.37 (m, 2H), 2.98 (m, 4H), 2.95 (s, 3H), 2.77 (m, 1H), 2.24 (s, 6H), 1.99 (m, 6H); $^{13}$C NMR (DMSO-d$_6$) δ167.5, 159.4, 155.7, 147.9, 146.0, 145.7, 140.2, 129.7, 127.7, 120.8, 119.2, 118.7, 118.4, 112.7, 111.8, 101.4, 55.0, 53.7, 52.0, 50.7, 45.4, 38.8, 38.5, 34.4, 29.8, 22.0, 15.2. Anal. Calcd for C$_{34}$H$_{44}$N$_4$O$_6$·HCl·H$_2$O: C, 61.95; H, 7.19; N, 8.50. Found: C, 62.18; H, 7.26; N, 8.44.

4. B is O

EXAMPLE 76

1,4-Dihydro-4-[3-[[[[3-[4-(3-methoxyphenyl)-1-piperidinyl]propyl]oxy]carbonyl]amino]phenyl]-2,6-dimethyl-3,5-pyridinedicarboxylic acid, dimethyl ester hydrochloride

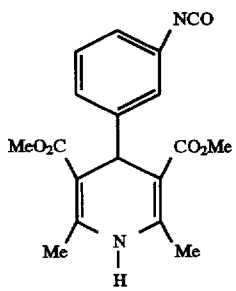

1

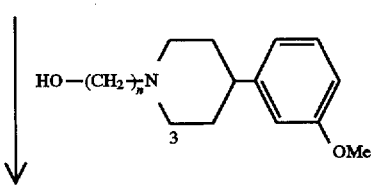

General Coupling Procedure

A solution of the isocyanate 1 (10 mmol) and the appropriate alcohol 3 (12 mmol) in CH$_2$Cl$_2$ (500 mL) was stirred for 3 h at room temperature. After concentration in vacuo, the residue was purified by chromatography (SiO$_2$: MeOH:CH$_2$Cl$_2$). This material was taken up in EtOAc and an equimolar quantity of 1N HCl in Et$_2$O was added in a dropwise fashion to form the salt. Additional Et$_2$O was subsequently added and the resulting precipitate collected by filtration and dried overnight to furnish the hydrochlorides salts. In this manner the following compound was obtained as a white solid in 64% yield: mp 120°–132° C.; $^1$H NMR (DMSO-d$_6$) δ10.69 (br s, 1H), 9.62 (s, 1H), 8.99 (s, 1H), 7.25 (m, 3H), 7.10 (t, 1H, J=7.5 Hz), 6.79 (m, 4H), 4.86 (s, 1H), 4.15 (t, 2H, J=6.0 Hz), 3.74 (s, 3H), 3.57 (m, 2H), 3.55 (s, 6H), 3.14 (m, 2H), 3.01 (m, 2H), 2.79 (m, 1H), 2.26 (s, 6H), 2.12 (m, 4H), 1.97 (m, 2H); $^{13}$C NMR (DMSO-d$_6$) δ167.8, 159.9, 153.6, 148.6, 146.2, 139.2, 130.0, 128.7, 121.5, 119.0, 117.5, 116.2, 113.0, 112.1, 101.6, 61.8, 55.3, 53.7, 52.4, 51.0, 38.7, 30.1, 23.7, 18.6. Anal. Calcd for C$_{33}$H$_{41}$N$_3$O$_7$·HCl·H$_2$O: C, 61.34; H, 6.86; N, 6.50. Found: C, 61.29; H, 6.85; N, 6.39.

As can be seen, the desired Formula I product may be obtained by appropriate selection of starting isocynate, amine or alcohol. One skilled in the art of organic synthesis would know how to select and react the required reagents to product the desired Formula I product.

Chart 1. Known, Non-Peptidic NPY Antagonists
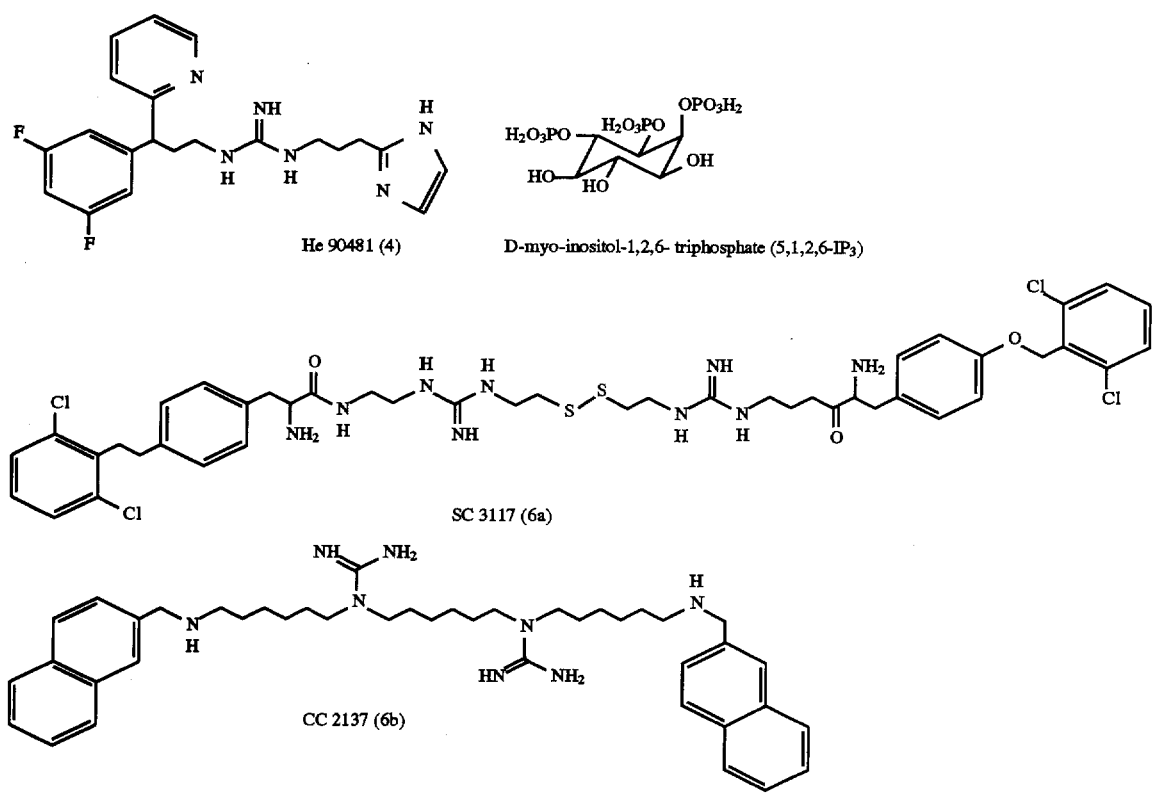
Scheme 1
General Processes for Compound (I) Synthesis: B is a Chemical Bond
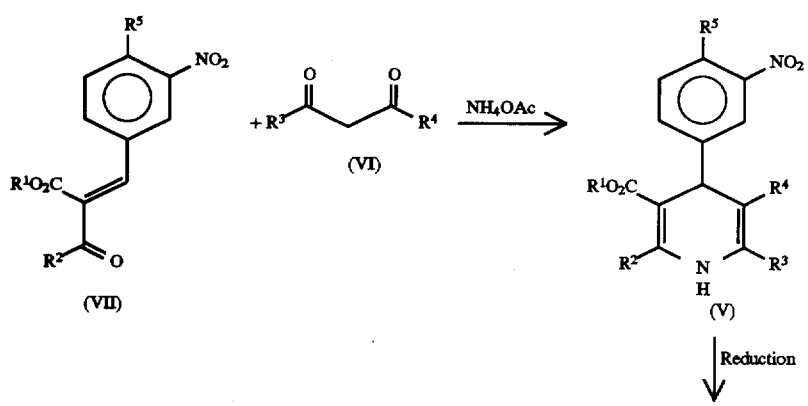

-continued
Scheme 1
General Processes for Compound (I) Synthesis: B is a Chemical Bond
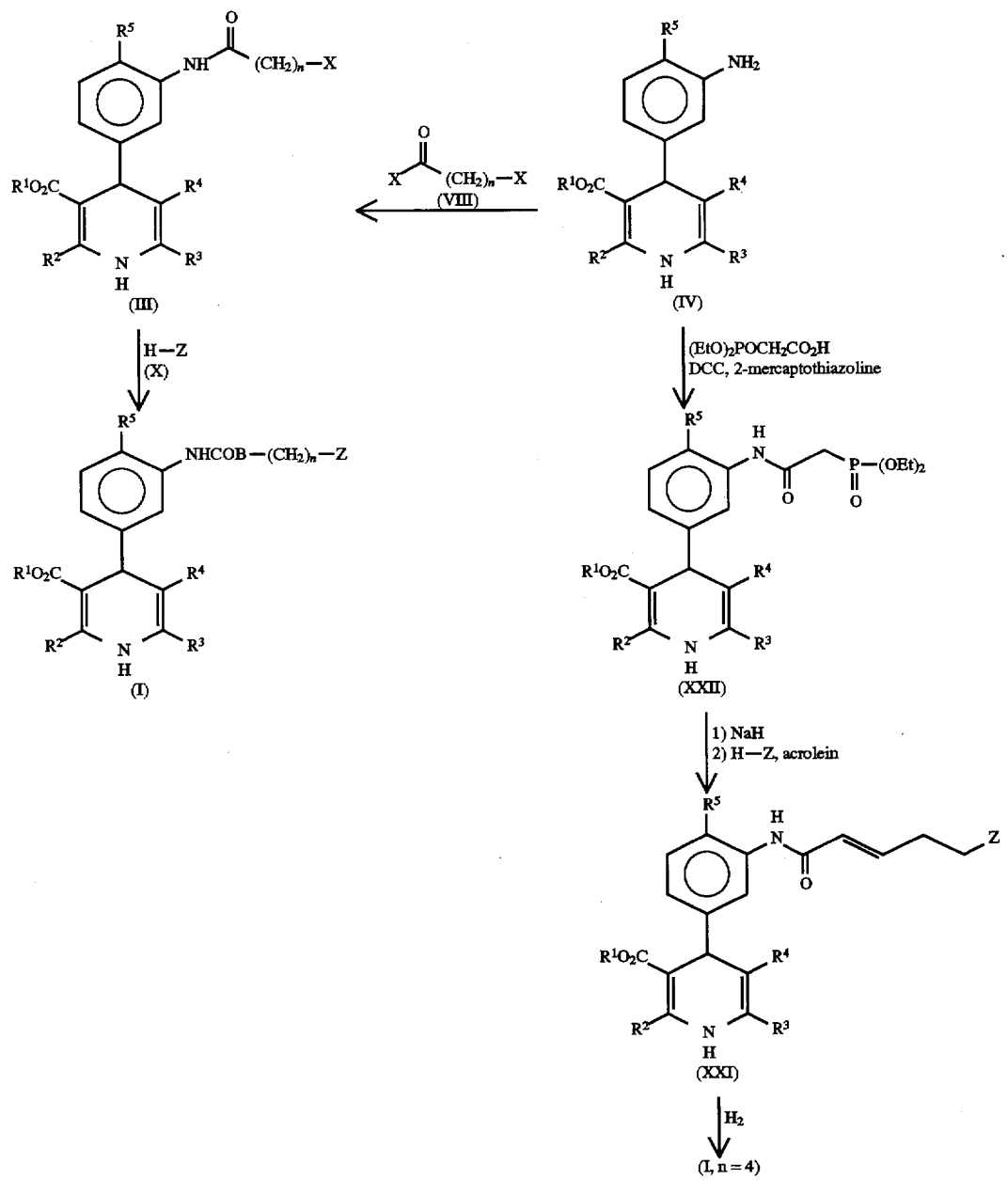

Scheme 2
General Processes for Compound (I) Synthesis: B is NH
A.
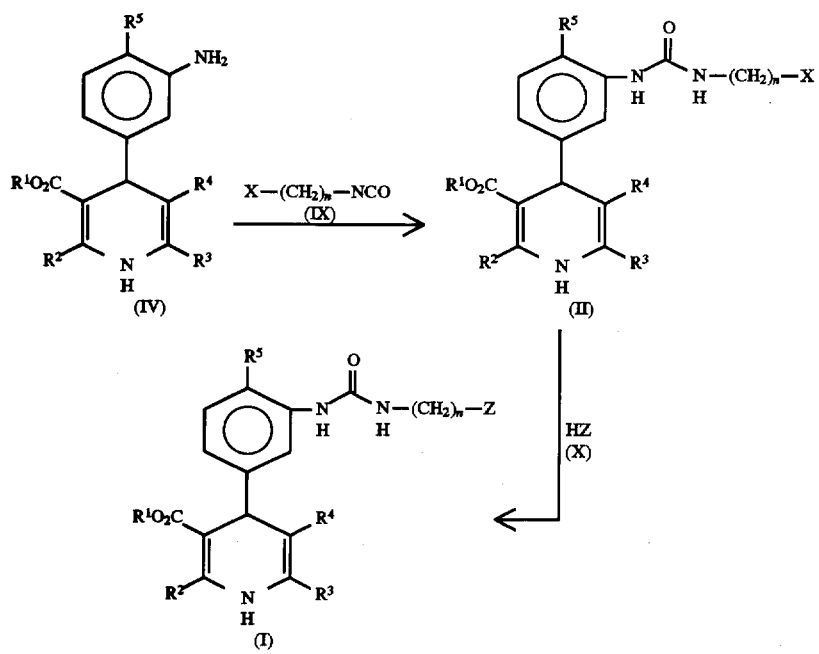
B.
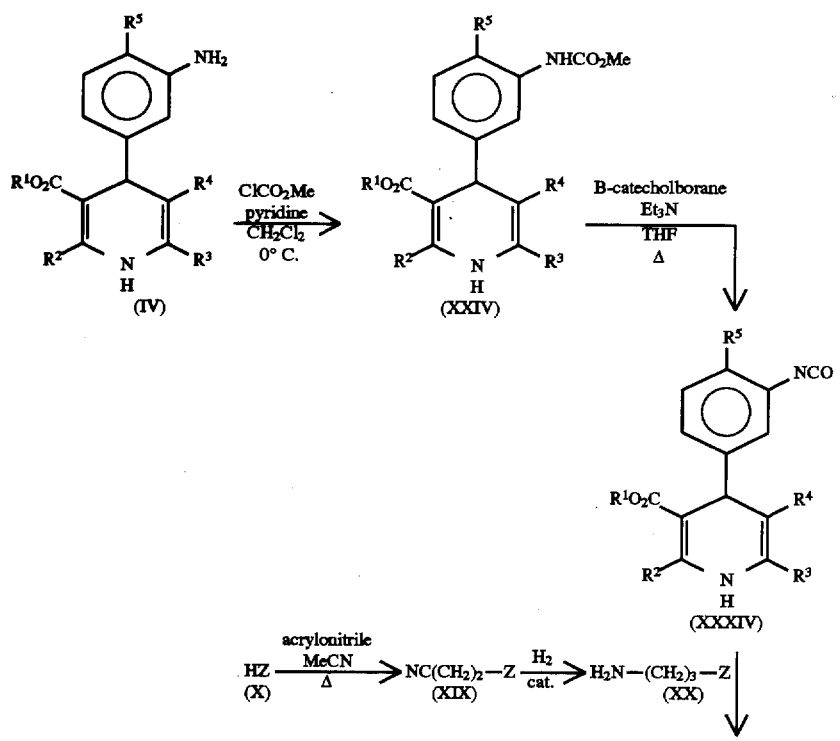

-continued
Scheme 2
General Processes for Compound (I) Synthesis: B is NH
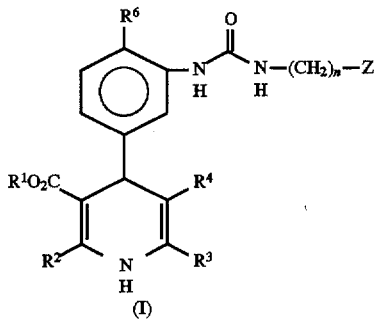
Scheme 3
Modified Processes for Compound (V) Synthesis
A. $R^2$ and/or $R^3$ = CN:
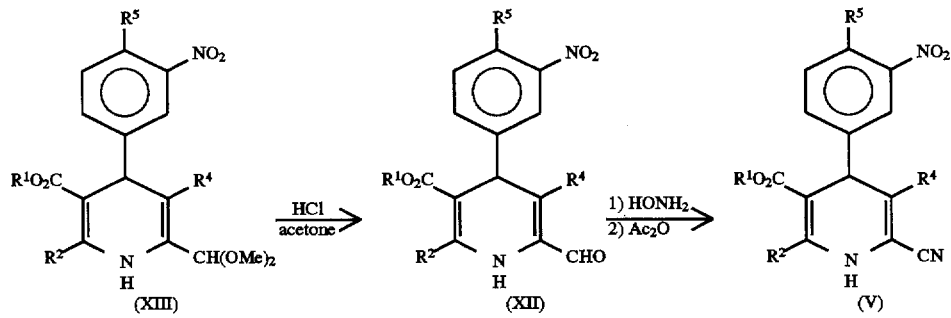
B. $R^4$ = 
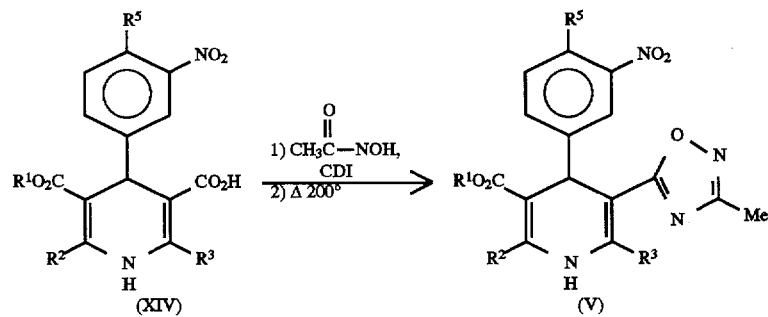

Scheme 4
Preparation of H-Z Compounds of Formula (X)
A. General Syntheses
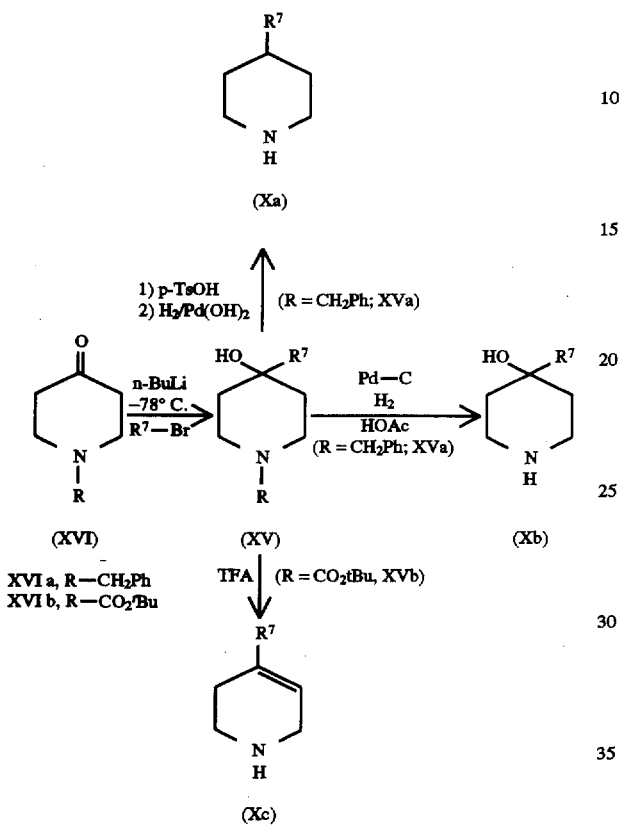
XVI a, R=CH₂Ph
XVI b, R=CO₂tBu
B. Specific Example Syntheses
1)
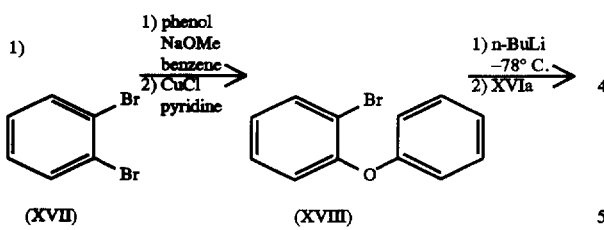
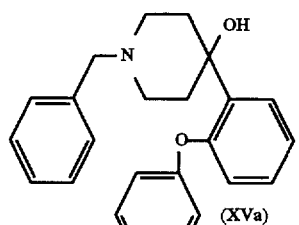
-continued
Scheme 4
Preparation of H-Z Compounds of Formula (X)
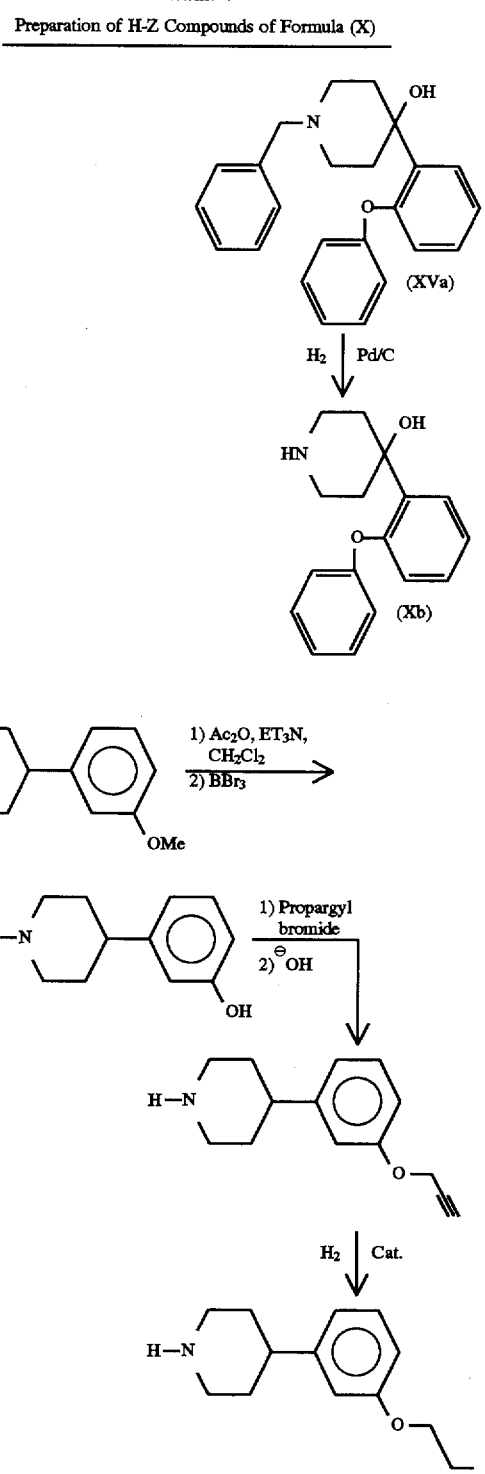

Scheme 5
Specific Syntheses for Selected Compounds of Formula I: $R^5$ = OH
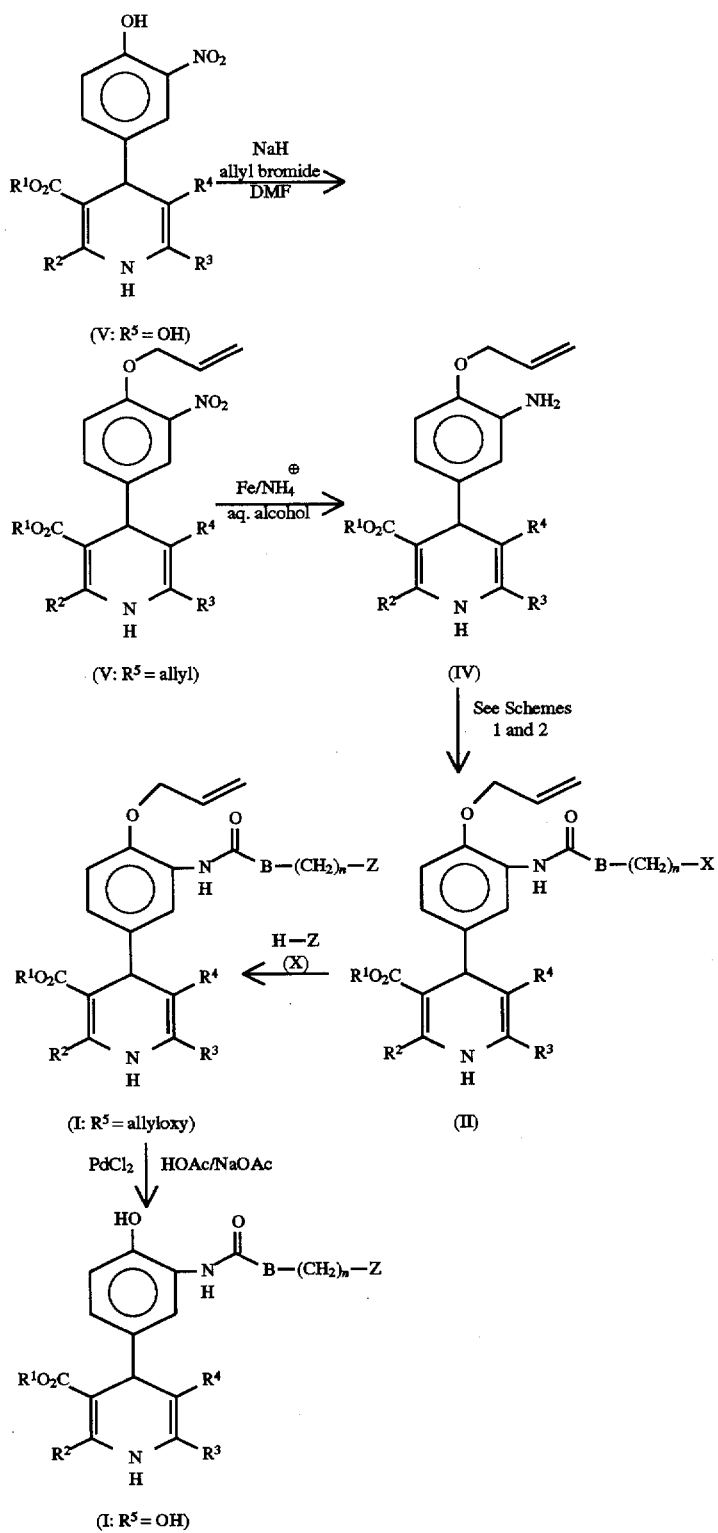

Scheme 6
Quaternization of Selected Formula I Compounds

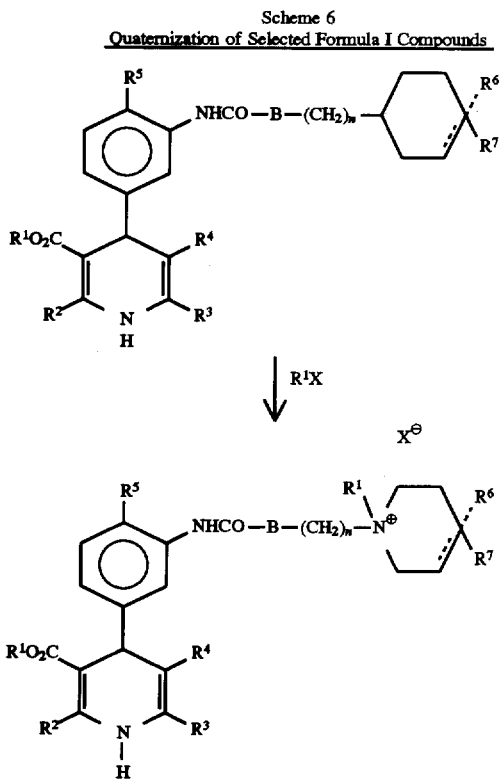

References and Notes

1. K. Takemoto, *Proc. Nat. Acad. Sci.*, 1982, 79, 5485–5489.
2. (a) D. R. Gehlert, *Life Sciences*, 1994, 55, 551–62. (b) L. Grundemar and R. Håkånson, *TiPS*, 1994, 15, 153–159. (c) C. Wahlestedt and D. J. Reis, *Ann. Rev. Pharmacol. Toxicol.*, 1993, 32, 309–352. (d) J. D. White, *Regulatory Peptides*, 1993, 49, 93–107. (e) A. Sahu and S. P. Kalra, *Trends Endocrinol. Metab.*, 1993, 4, 217–224. (f) Y. Dumont, J. C. Martel, A. Fournier, S. St. Pierre and R. Quirion, *Prog. Neurobiol.* 1992, 38, 125–167. (g) M. C. Michel and A. Buscher, *Drugs of the Future*, 1992, 17, 39–45. (h) M. C. Michel, *TiPS*, 1991, 12, 389–394. (i) J. Lehmann, *Drug. Dev. Res.*, 1990, 19, 329–351. (j) G. Williams, *Peptides*, 1995, 4, 757–71.
3. M. C. Michel and H. J. Motulsky, *Annu. Rev. N.Y. Acad. Sci.*, 1990, 611, 392–394; U. S. Pat. No. 4,912,119, 1990 (Heumann Pharma GMBH).
4. L. Edvinsson, M. Adamsson and I. Jansen, *Neuropeptides*, 1990, 17, 99–105.
5. (a) M. B. Doughty, C. Chaurasia and K. Li, *J. Med. Chem.*, 1993, 36, 272–79. (b) M. B. Doughty, S. S. Chu, G. A. Misse and R. Tessel, *BioMed. Chem. Lett.*, 1992, 2, 1497–1502. (c) C Chaurasia, G. Misse, R. Tessel and M. B. Doughty, *J. Med. Chem.*, 1994, 37, 2242–48.
6. (a) A. Sausins and G. Duburs, *Heterocycles*, 1988, 27, 269. (b) D. M. Stout and A. I. Meyers, *Chem. Review*, 1982, 82, 223. (c) J. Kuthan and A. Kurfurst, *Ind. Eng. Chem. Prod. Res. Dev.*, 1982, 21, 191. (d) U. Eisner and J. Kuthan, *J. Chem. Rev.*, 1972, 72, 1. (e) J. Prous, P. Biancafort, J. Castañer, M. N. Serradell and N. Mealy, *Drugs of the Future*, 1981, 6, 427.
7. G. Jones, *Org. Reactions*, 1967, 15, 204.
8. (a) V. H. Meyer, F. Bossert, E. Wehinger, K. Stoepel and W. Vater, *Arzneim.-Forsch/Drug Research*, 1981, 31, 407. (b) A. F. Joslyn, E. Luchowski, D. J. Triggle, *J. Med. Chem.*, 1988, 31, 1489–1492. (c) R. A. Coburn, M. Wierzba, M. J. Suto, A. J. Solo, A. M. Triggle, D. J. Triggle, *J. Med. Chem.*, 1988, 31, 2103, 2107. (d) E. Wehinger, U. S. Pat. No. 4,920,255, 1981. (e) U. Rosentreter, *Synthesis*, 1985, 210. (f) F. Bossert, H. Horstmann, H. Meyer, W. Vater, *Arzneim.-Forsch.*, 1979, 29, 226–229. (g) *Chem. Abstr.*, 1985, 103, 123313g.
9. N. M. Yoon and J. S. Choi, *S. Synlett*, 1993, 135–136.
10. D. Scherling, W. Karl, A. J. Ahr, A. Kern and H. M. Siefert, *Arzneim.-Forsch.*, 1991, 41, 1009–1021.
11. Y. Satoh, et al, *Chem. Pharm. Bull.*, 1991, 39, 3189–3201.
12. A. L. Williams, R. E. Kinney and R. F. Bridger, *J. Org. Chem.*, 1967, 32, 2501–5.
13. C. Wahlestedt and D. J. Reis, *Annual Rev. Pharmacol. Toxicol.*, 1993, 32, 309–52; p. 331.
14. E. Wehinger, U. S. Pat. No. 4,920,255, 1981.
15. K. Ramadas and N. Srinivasan, *Syn. Commun.*, 1992, 22, 3189–3195.
16. V. L. K. Valli and H. Alper, *J. Org. Chem.*, 1995, 60, 257–258.
17. G. A. Loew, et al., *Mol. Pharmacol.*, 1988, 34, 363–376.
18. (a) I. Von Wijngaarten, et al., *J. Med. Chem.*, 1988, 31, 1934–1940. (b) G. Frenking, et al., *J. Life Sci. Div.*, 1986, 75, 53–56. (c) B. E. Evans, et al., *J. Med. Chem.*, 1992, 35, 3919–3927. (d) A. I. Meyers, et al., *J. Am. Chem. Soc.*, 1984, 106, 3270–3276.
19. M. Dahlgard and R. Q. Brewster, *J. Am. Chem. Soc.*, 1958, 80, 5861–5863.
20. Y. Nagao, et al., *Chem. Pharm. Bull.*, 1984, 32, 4686–4689.

We claim:

1. A compound of Formula I and its pharmaceutically acceptable acid addition salts or hydrates thereof, wherein $R^1$ is lower alkyl;

$R^2$ and $R^3$ are independently selected from cyano and lower alkyl;

$R^4$ is selected from —$CO_2R^1$, cyano and $R^5$ is selected from hydrogen, halogen, hydroxy, lower alkyl, lower alkenyloxy, and lower alkoxy;

B is —NH—, —$NR^1$—, —O— or a covalent bond except when $R^4$ is cyano;

n is an integer selected from 2 to 5; and

Z is

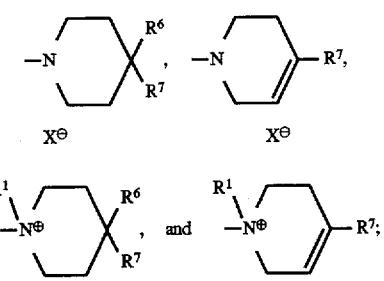

$R^6$ is hydrogen, hydroxy or cyano; and
$R^7$ is $C_{3-7}$ cycloalkyl,

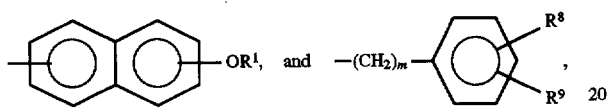

with m being zero or an integer from 1 to 4; and
$R^8$ and $R^9$ being independently selected from hydrogen, lower alkyl, $C_{3-7}$ cycloalkyl, lower alkoxy, lower alkenyloxy, lower alkynyloxy, hydroxy, phenyl, phenoxy, $NH_2$, $NHCOR^1$, $CO_2R^1$, $NO_2$ and trifluoromethyl.

2. A compound of claim 1 wherein B is —NH— or —$NR^1$—.
3. A compound of claim 1 wherein B is a covalent bond.
4. A compound of claim 1 wherein B is —O—.
5. A compound of claim 1 wherein $R^7$ is

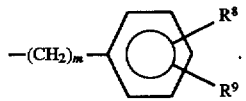

6. A compound of claim 1 wherein n is 3.
7. A compound of claim 2 wherein Z is

selected from 1,4-Dihydro-[3-[[[[3-[4-(3-methoxyphenyl)-1-piperidinyl]propyl]amino]carbonyl]amino]phenyl]-2,6-dimethyl-3,5-pyridinedicarboxylic acid, dimethyl ester;

1,4-Dihydro-4-[3-[[[[3-[4-hydroxy-4-(3-methoxyphenyl)piperidin-1-yl]propyl]amino]carbonyl]amino]phenyl]-2,6-dimethyl-3,5-pyridine dicarboxylic acid, dimethyl ester;

1,4-Dihydro-4-[3-[[[[3-[4-(2-methoxyphenyl)piperidin-1-yl]propyl]amino]carbonyl]amino]phenyl]-2,6-dimethyl-3,5-pyridine dicarboxylic acid, dimethyl ester;

1,4-Dihydro-4-[3-[[[[3-(4-phenylpiperidin-1-yl)propyl]amino]carbonyl]amino]phenyl]-2,6-dimethyl-3,5-pyridinedicarboxylic acid, dimethyl ester;

1,4-Dihydro-4-[3-[[[[3-(4-hydroxy-4-phenylpiperidin-1-yl)propyl]amino]carbonyl]amino]phenyl]-2,6-dimethyl-3,5-pyridine dicarboxylic acid, dimethyl ester;

1,4-Dihydro-2,6-dimethyl-4-[3-[[[[3-[4-[3-(2-propynyloxy)phenyl]-1-piperidinyl]propyl]amino]carbonyl]amino]phenyl]-3,5-pyridinedicarboxylic acid, dimethyl ester;

1,4-Dihydro-4-[3-[[[[3-[4-cyano-4-phenylpiperidin-1-yl]propyl]amino]carbonyl]amino]phenyl]-2,6-dimethyl-3,5-pyridine dicarboxylic acid, dimethyl ester;

1,4-Dihydro-4-[3-[[[[3-[4-(3-hydroxyphenyl)piperidin-1-yl]propyl]amino]carbonyl]amino]phenyl]-2,6-dimethyl-3,5-pyridine dicarboxylic acid, dimethyl ester;

1,4-Dihydro-4-[3-[[[[3-[4-naphthalen-1-ylpiperidin-1-yl]propyl]amino]carbonyl]amino]phenyl]-2,6-dimethyl-3,5-pyridine dicarboxylic acid, dimethyl ester;

4-[3-[[[[3-[4-(1,1'-Biphenyl-3-yl)piperidin-1-yl]propyl]amino]carbonyl]amino]phenyl]-1,4-dihydro-2,6-dimethyl-3,5-pyridine dicarboxylic acid, dimethyl ester;

1,4-Dihydro-4-[3-[[[[3-[4-(phenylmethyl)-piperidin-1-yl]propyl]amino]carbonyl]amino]phenyl-2,6-dimethyl-3,5-pyridinedicarboxylic acid, dimethyl ester;

4-[3-[[[[3-(4-cyclohexyl-1-piperidinyl)propyl]amino]carbonyl]amino]phenyl]-1,4-dihydro-2,6-dimethyl-3,5-pyridinedicarboxylic acid, dimethyl ester;

1,4-dihydro-4-[3-[[[[3-[4-hydroxy-4-(2-phenoxyphenyl)-1-piperidinyl]propyl]amino]carbonyl]amino]phenyl]-2,6-dimethyl-3,5-pyridinedicarboxylic acid, dimethyl ester;

1,4-Dihydro-4-[3-[[[[3-(4-phenyl-1-piperidinyl)propyl]amino]carbonyl]amino]phenyl]-2,6-dimethyl-3,5-pyridinedicarboxylic acid, ethyl methyl ester;

1,4-Dihydro-4-[3-[[[[3-[(4-phenylmethyl)-1-piperidinyl]propyl]amino]carbonyl]amino]phenyl]-2,6-dimethyl-3,5-pyridinedicarboxylic acid, ethyl methyl ester;

1,4-Dihydro-4-[3-[[[3-[4-hydroxy-4-(2-methoxyphenyl)-piperidin-1-yl]propyl]amino]carbonyl]amino]phenyl]-2,6-dimethyl-3,5-pyridinedicarboxylic acid, ethyl methyl ester;

1,4-Dihydro-4-[3-[[[[3-[4-hydroxy-4-(3-methoxyphenyl)-piperidin-1-yl]propyl]amino]carbonyl]amino]phenyl]-2,6-dimethyl-3,5-pyridinedicarboxylic acid, ethyl methyl ester;

1,4-Dihydro-2,6-dimethyl-4-[3-[[[[3-[4-[3-(2-propoxy)phenyl]-1-piperidinyl]-propyl]amino]carbonyl]amino]phenyl]3,5-pyridinedicarboxylic acid, dimethyl ester;

1,4-Dihydro-4-[3-[[[[2-[4-(3-methoxyphenyl)-1-piperidinyl]ethyl]amino]carbonyl]amino]phenyl]-2,6-dimethyl-3,5-pyridinedicarboxylic acid, dimethyl ester hydrochloride;

1,4-Dihydro-4-[3-[[[[4-[4-(3-methoxyphenyl)-1-piperidinyl]butyl]amino]carbonyl]amino]phenyl]-2,6-dimethyl-3,5-pyridinedicarboxylic acid, dimethyl ester hydrochloride;

1,4-Dihydro-4-[3-[[[[3-[4-(3-methoxyphenyl)-1-piperidinyl]propyl]methylamino]carbonyl]amino]phenyl]-2,6-dimethyl-3,5-pyridinedicarboxylic acid, dimethyl ester hydrochloride.

8. A compound of claim 2 wherein Z is

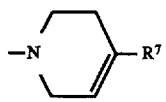

selected from 1,4-Dihydro-4-[3-[[[[3-[1,2,3,6-tetrahydro -4-(3-methoxyphenyl)pyridin-1-yl]propyl]amino]carbonyl] amino]phenyl]-2,6-dimethyl-3,5-pyridine dicarboxylic acid, dimethyl ester;

1,4-Dihydro-4-[3-[[[[3-(1,2,3,6-tetrahydro-4-phenylpyridin-1-yl)propyl]amino]carbonyl]amino] phenyl]-2,6-dimethyl-3,5-pyridine dicarboxylic acid, dimethyl ester;

1,4-Dihydro-4-[3-[[[[3-[1,2,3,6-tetrahydro-4-(3-hydroxyphenyl)pyridine]propyl]amino]carbonyl] amino]phenyl]-2,6-dimethyl-3,5-pyridine dicarboxylic acid, dimethyl ester;

1,4-Dihydro-4-[3-[[[3-[1,2,3,6-tetrahydro-4-(1-naphthalenyl)-1-pyridinyl]propyl]amino]carbonyl] amino]phenyl]-2,6-dimethyl-3,5-pyridinedicarboxylic acid, dimethyl ester.

9. A compound of claim 3 selected from 1,4-Dihydro-4-[3-[[3-(4-phenylpiperidin-1-yl)-1-oxo-1-propyl]amino]phenyl]-2,6-dimethyl-3,5-pyridinedicarboxylic acid, dimethyl ester;

1,4-Dihydro-4-[3-[[4-(4-phenylpiperidin-1-yl)-1-oxo-1-butyl]amino]phenyl]-2,6-dimethyl-3,5-pyridinedicarboxylic acid, dimethyl ester;

1,4-Dihydro-4-[3-[[5-(4-phenylpiperidin-1-yl)-1-oxo-1-pentyl]amino]phenyl]-2,6-dimethyl-3,5-pyridinedicarboxylic acid, dimethyl ester;

1,4-Dihydro-4-[3-[[6-(4-phenylpiperidin-1-yl)-1-oxo-1-hexyl]amino]phenyl]-2,6-dimethyl-3,5-pyridinedicarboxylic acid, dimethyl ester;

1,4-Dihydro-4-[3-[[5-(4-hydroxy-4-phenylpiperidin-1-yl)-1-oxo-1-pentyl]amino]phenyl]-2,6-dimethyl-3,5-pyridinedicarboxylic acid, dimethyl ester;

1,4-Dihydro-4-[3-[[5-(4-cyano-4-phenylpiperidin-1-yl)-1-oxo-1-pentyl]amino]phenyl]-2,6-dimethyl-3,5-pyridinedicarboxylic acid, dimethyl ester;

1,4-Dihydro-4-[3-[[[4-[4-(3-methoxyphenyl)-1-piperidinyl]butyl]carbonyl]amino]phenyl]-2,6-dimethyl-3,5-pyridinedicarboxylic acid, dimethyl ester.

10. The compound of claim 4, 1,4-dihydro-4-[3-[[[3-[4-(3-methoxyphenyl)-1-piperidinyl]propyl]oxy]carbonyl] amino]phenyl]-2,6-dimethyl-3,5-pyridinedicarboxylic acid, dimethyl ester hydrochloride.

11. A compound of claim 7 selected from 1,4-Dihydro-4-[3-[[[3-[4-(3-methoxyphenyl)piperidin-1-yl]propyl]amino]carbonyl]amino]phenyl]-2,6-dimethyl-3,5-pyridinedicarboxylic acid, dimethyl ester;

1,4-Dihydro-4-[3-[[[3-[4-(2-methoxyphenyl)piperidin-1-yl]propyl]amino]carbonyl]amino]phenyl]-2,6-dimethyl-3,5-pyridinedicarboxylic acid, dimethyl ester;

1,4-Dihydro-4-[3-[[[3-[4-(3-hydroxyphenyl)piperidin-1-yl]propyl]amino]carbonyl]amino]phenyl]-2,6-dimethyl-3,5-pyridinedicarboxylic acid, dimethyl ester;

1,4-Dihydro-4-[3-[[[3-[4-naphthalenylpiperidin-1-yl] propyl]amino]carbonyl]amino]phenyl]-2,6-dimethyl-3,5-pyridinedicarboxylic acid, dimethyl ester;

4-[3-[[[[3-(4-cyclohexyl-1-piperidinyl)propyl]amino] carbonyl]amino]phenyl]-1,4-dihydro-2,6-dimethyl-3, 5-pyridinedicarboxylic acid, dimethyl ester.

12. A compound of claim 8 selected from 1,4-Dihydro-4-[3-[[[[3-[1,2,3,6-tetrahydro-4-(3-methoxyphenyl)pyridin-1-yl]propyl]amino]carbonyl] amino]phenyl]-2,6-dimethyl-3,5-pyridinedicarboxylic acid, dimethyl ester;

1,4-Dihydro-4-[3-[[[3-[1,2,3,6-tetrahydro-4-(1-naphthalenyl)pyridin-1-yl]propyl]amino]carbonyl] amino]phenyl-2,6-dimethyl-3,5-pyridinedicarboxylic acid, dimethyl ester.

13. A compound of claim 2 wherein Z is

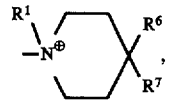

1-[3-[[[[1,4-Dihydro-3,5-bis(methoxycarbonyl)-2,6-dimethyl-4-pyridinyl]phenyl]amino]carbonyl]amino] propyl]-4-(3-methoxyphenyl)-1-methylpiperidinium iodide.

14. A method of promoting weight loss and treating eating disorders in a mammal which comprises administering to a mammalian host an anorexiant effective dose of a compound claimed in claim 1.

15. A pharmaceutical composition for use in promoting weight loss and treating eating disorders, wherein the composition comprises an anorexiant effective amount of a compound claimed in claim 1 in combination with a pharmaceutically acceptable carrier.

* * * * *